US012544586B2

(12) United States Patent
Li et al.

(10) Patent No.: US 12,544,586 B2
(45) Date of Patent: Feb. 10, 2026

(54) HAIR REMOVAL DEVICE AND PELTIER COOLER

(71) Applicant: SHENZHEN JVK MEDICAL INSTRUMENTS CO., LTD., Shenzhen (CN)

(72) Inventors: Bing Li, Shenzhen (CN); Fengqiu Zhao, Shenzhen (CN)

(73) Assignee: SHENZHEN JVK MEDICAL INSTRUMENTS CO., LTD., Shenzhen (CN)

(*) Notice: Subject to any disclaimer, the term of this patent is extended or adjusted under 35 U.S.C. 154(b) by 660 days.

(21) Appl. No.: 17/916,585

(22) PCT Filed: Aug. 20, 2020

(86) PCT No.: PCT/CN2020/110358

§ 371 (c)(1),
(2) Date: Apr. 6, 2023

(87) PCT Pub. No.: WO2021/196506

PCT Pub. Date: Oct. 7, 2021

(65) Prior Publication Data

US 2024/0285967 A1 Aug. 29, 2024

(30) Foreign Application Priority Data

Apr. 2, 2020 (CN) ......................... 202020474507.1
Apr. 2, 2020 (CN) ......................... 202020475246.5
Jul. 16, 2020 (CN) ........................ 202021411222.X

(51) Int. Cl.
*A61N 5/06* (2006.01)
*A61N 5/00* (2006.01)
*H10N 10/13* (2023.01)

(52) U.S. Cl.
CPC ........... *A61N 5/0617* (2013.01); *H10N 10/13* (2023.02); *A61N 2005/007* (2013.01)

(58) Field of Classification Search
CPC ...... A61N 5/0617; A61N 5/0616; A61N 5/06; A61N 2005/007; A61N 2005/005;
(Continued)

(56) References Cited

U.S. PATENT DOCUMENTS 5,072,289 A * 12/1991 Sugimoto ............. H01L 21/486 257/737
6,273,885 B1 8/2001 Koop et al.
(Continued)

FOREIGN PATENT DOCUMENTS

CN 203970545 U 12/2014
CN 203988359 U 12/2014
(Continued)

*Primary Examiner* — Nathan J Jenness
(74) *Attorney, Agent, or Firm* — Cheng-Ju Chiang

(57) ABSTRACT

The present invention relates to a hair removal device and a Peltier cooler. The hair removal device comprises a hair removal head, a light source assembly, a power supply unit, and a control circuit board; the power supply unit supplies power to the light source assembly, and the control circuit board controls the light source assembly to generate pulsed light; a transparent medium body is mounted on the hair removal work head to serve as a hair removal work surface coming into contact with skin so as to form a transparent medium hair removal work surface. The Peltier cooler comprises a semiconductor pillar layer, and a hot surface and
(Continued)

a cold surface at two ends of the semiconductor galvanic couple layers; the cold surface is a transparent crystal so as to form a transparent crystal cold surface.

13 Claims, 15 Drawing Sheets

(58) Field of Classification Search
CPC .................... H10N 10/13; F25B 21/02; A61B 2018/00047; A61B 2018/00476; A61B 18/18
USPC ................................................ 606/2; 607/88
See application file for complete search history.

(56) References Cited

U.S. PATENT DOCUMENTS

| | | | | |
|---|---|---|---|---|
| 2004/0093042 | A1* | 5/2004 | Altshuler | A61B 18/203 607/88 |
| 2004/0176754 | A1* | 9/2004 | Island | A61B 18/203 606/9 |
| 2006/0052847 | A1* | 3/2006 | Davenport | A61B 18/203 607/88 |
| 2011/0040235 | A1* | 2/2011 | Castel | A61F 7/00 604/20 |
| 2017/0023281 | A1* | 1/2017 | Fromm | B01L 7/52 |
| 2017/0367761 | A1* | 12/2017 | Beerwerth | A61B 18/20 |
| 2021/0123641 | A1* | 4/2021 | Monazami | F28D 15/046 |

FOREIGN PATENT DOCUMENTS

| | | | | | |
|---|---|---|---|---|---|
| CN | 206355031 | U | | 7/2017 | |
| CN | 208114942 | U | | 11/2018 | |
| CN | 110151307 | A | | 8/2019 | |
| CN | 209316830 | U | | 8/2019 | |
| CN | 209464502 | U | | 10/2019 | |
| CN | 110403695 | A | | 11/2019 | |
| CN | 209572304 | U | | 11/2019 | |
| CN | 209826966 | U | | 12/2019 | |
| CN | 110755153 | A | | 2/2020 | |
| CN | 210114495 | U | | 2/2020 | |
| JP | H7-139750 | A | | 5/1995 | |
| JP | H07139750 | | * | 5/1995 | F24F 1/00 |
| JP | H9-129937 | A | | 5/1997 | |
| JP | 2002-172178 | A | | 6/2002 | |
| JP | 2004-159666 | A | | 6/2004 | |
| JP | 2005-319209 | A | | 11/2005 | |
| JP | 2009-141079 | A | | 6/2009 | |
| JP | 2010-75420 | A | | 4/2010 | |
| JP | 2012-502723 | A | | 2/2012 | |
| JP | 2015-139700 | A | | 8/2015 | |
| WO | 2008/146689 | A1 | | 12/2008 | |
| WO | 2012/140800 | A1 | | 10/2012 | |
| WO | WO 2015098427 | | * | 12/2013 | A45D 26/00 |
| WO | 2015/098427 | A1 | | 7/2015 | |
| WO | 2018/154758 | A1 | | 8/2018 | |

* cited by examiner

HAIR REMOVAL DEVICE AND PELTIER COOLER

BACKGROUND OF THE INVENTION

CROSS REFERENCE TO RELATED APPLICATIONS

The present invention is a 35 U.S.C. § 371 National Phase conversion of International (PCT) Patent Application No. PCT/CN2020/110358, filed on Aug. 20, 2020, which claims benefit of Chinese Application No. 202020475246.5, filed on Apr. 2, 2020, Chinese Application No. 202020474507.1, filed on Apr. 2, 2020, and Chinese Application No. 202021411222.X, filed on Jul. 16, 2020, the disclosure of which is incorporated by reference herein. The PCT International Patent Application was filed and published in Chinese.

Field of the Invention

The present invention relates to Peltier cooler technology, especially relates to a hair removal device and Peltier cooler.

Description of Related Art

The head of the present hair removal device on the market cannot provide an ice cooling effect. The light source and heatsink in the hair removal device dissipate heat though air entering the air inlet provided on the front of the light source and heatsink; where heat dissipation is slow, the cooling effect is not good, the experience is not good, hair removal efficiency and hair removal effect are low; and there are water mist or water droplets in the device, which will damage the control board.

BRIEF SUMMARY OF THE INVENTION

The object of the present invention is to provide a hair removal device, which aims to overcome that the head of the existing hair removal device cannot form an ice-cooling effect and the experience is not good.

Another object of the present invention is to provide a Peltier cooler.

To obtain the above object, the present invention provides:

- a hair removal device comprises a head for hair removal, a light source assembly, a power supply unit, and a control circuit board; wherein the power supply unit supplies power to the light source assembly, and the control circuit board controls the light source assembly to emit pulsed light; the head for hair removal is equipped with a transparent body to form a transparent working surface in contact with skin for hair removal; the pulse light emitted from the light source assembly is transmitted from the transparent body to perform hair removal; the transparent body is cooled by a heat dissipation assembly for a cooling effect to skin or pre-cooling skin to be depilated.

In some embodiments, the transparent working surface is located at a front end of the head, and forms a whole front-end surface in contact with skin for cooling; the transparent body is attached to a cooler, or the transparent body forms the cooler; the heat dissipation assembly is used for the cooler to dissipate heat.

In some embodiments, the cooler is a Peltier cooler; the Peltier cooler comprises a hot side and a cold side; the Peltier cooler uses the transparent body as the cold side to obtain a transparent cold side; or, the cold side of the Peltier cooler is attached to the transparent body and cooled the transparent body; the hot side of the Peltier cooler is connected to the heat dissipation assembly for heat dissipation; the hair removal device comprises a housing, and the light source assembly, the power supply unit, the control circuit board and the heat dissipation assembly are installed in the housing; the transparent body is installed in a head housing; the housing defines air inlets and air outlets; the heat dissipation assembly comprises a heatsink and a fan; the heatsink is arranged in an air path communicate the air inlets, the fan and the air outlets for heat dissipation.

In some embodiments, the Peltier cooler has a light-transmitting region, which is used for pulse light transmission for hair removal; the light-transmitting region is a hollow region in the Peltier cooler, and/or, the light-transmitting region is provided by the transparent body of the Peltier cooler; the Peltier cooler comprises a semiconductor pillar layer, and the hot side and the cold side are respectively fixed on opposite ends of the semiconductor pillar layer; the transparent body is fixedly installed in an annular edge of the head housing.

In some embodiments, the cold side and/or the hot side of the Peltier cooler is made of a ceramic material so as to form the ceramic cold side and/or the ceramic hot side; or, the cold side and/or hot side of the Peltier cooler are made from transparent materials to form a transparent cold side and/or a transparent hot side; the control circuit board controls the light source assembly to emit pulsed light which transmits through the light-transmitting region of the Peltier cooler, further transmits the transparent working surface for hair removal on the skin in contact with the working surface; the semiconductor pillar layer, the hot side and the cold side of the Peltier cooler together define the hollow region; the Peltier cooler is annular with a hollow region inside as the light-transmitting region; the Peltier cooler is fixed in the head housing, and is attached to a back of the transparent body.

In some embodiments, the heat dissipation assembly comprises a heat pipe, the heat pipe is connected with the hot side of the Peltier cooler and the heatsink, and is used to quickly transport heat from the hot side to the heatsink for heat dissipation; the heatsink is one or more of: plate fin heatsinks, plate fins or thermally conductive plates; wherein plate fins are set as one or more groups; the heat pipe is inserted in or fixed on a top of the plate fins or thermally conductive plates; refrigerant is filled inside the heat pipe; the heat pipe is in contact with the hot side or connect the hot side through a thermally conductive member; the thermally conductive member or a section of the heat pipe is configured corresponding to the hot side of the Peltier cooler, and is in contact with the hot side; the fan is installed inside or outside a cavity, and the cavity extends to form an air outlet channel, and an end of the air outlet channel is connected with the air outlet.

In some embodiments, the air inlet in the housing, air ducts of the light source assembly, the fan, and the air outlet are in air communication to form an air path for a light source assembly to dissipate heat; when the fan starts, cold air enters from the air inlet to take heat from the light source assembly, and is discharged by fan from the air outlet for cooling the light source assembly; a plurality of air inlets comprises a first air inlet in the housing corresponding to the heatsink, and second air inlets in the housing arranged corresponding to the light source assembly; the first air inlet is used for cold air entering into the air ducts of the heatsink; the second air inlet is used for cold air entering the air path for the light source assembly and is in air communication with the light source assembly; the light source assembly comprises a light source and a reflector outside the light source; an air guide cover is arranged outside the reflector, and a space between the air guide cover and the reflector is in air communication with the air path for the light source assembly; and the reflector is made of thermally conductive material.

In some embodiments, the light source assembly comprises a heat dissipation assembly; the heat dissipation assembly comprises a heat pipe, a heatsink, and a fan; the heat pipe is thermally connected between the light source assembly and the heatsink, and dissipates heat from the light source assembly to the heatsink; the heatsink for the light source assembly is arranged in an air path which is in air communication with the air inlet, the fan and the air outlet; and the light source heatsink is cooled through the air path; the light source assembly comprises a light source and a reflector outside the light source; heat from the light source is transferred to the reflector for heat dissipation; the light source assembly further comprises a thermally conductive cover; one side of the thermally conductive cover is attached to the reflector, and the other side is provided with a tubular slot; a section of the heat pipe is fitted in the tubular slot so as to transfer heat to the heat pipe; or, the reflector is provided with a tubular slot, and a section of the heat pipe is fitted in the tubular slot so as to transfer heat to the heat pipe.

In some embodiments, the cold side is a transparent crystal to form a transparent crystal cold side; the transparent crystal connects one or more sets of the semiconductor pillar layers each with one hot side connected thereto; the Peltier cooler has a light-transmitting region provided by the transparent crystal; the transparent crystal cold side is the transparent working surface.

Preferably, the transparent is a transparent crystal. In some embodiment, the cooler is annular, and a hollow region is defined inside as a light-transmitting region for pulsed light to be transmitted for hair removal.

Further, the cooler is an annular Peltier cooler; the semiconductor pillar layer is annular, and electronic components are arranged in an annular region; the hot side and the cold side are annular corresponding to the semiconductor pillar layer; and the hot side and the cold side are ceramic substrates and the hot side of the ceramic substrate.

In some embodiments, the head is equipped with at least two sensors for determining whether the working surface is completely or almost completely covered by skin so as to turn on/off the light source; the two sensors are installed at opposite corners along a diagonal line of the working surface.

The present invention also provides a Peltier cooler, which comprising a semiconductor pillar layer and a hot side and a cold side at opposite ends of the semiconductor pillar layer; wherein the cold side is a transparent crystal to form a transparent crystal cold side; the transparent crystal connects one or more sets of the semiconductor pillar layers each connecting one hot side; the Peltier cooler has a light-transmitting region; the light-transmitting region is provided by the transparent crystal; the Peltier cooler provides a cooling work surface for the hair removal device for a cooling effect to skin or pre-cooling skin to be depilated.

Further, the one or more sets of the semiconductor pillar layers each connected with one hot side are arranged on sides of the transparent crystal; the semiconductor pillar layer comprises a semiconductor pillars and metal conductors connected thereto; the hot side and the transparent crystal cold side of are fixedly connected to the metal conductors of the semiconductor pillar layer; the hot side and the transparent crystal cold side are soldered with the metal conductors.

Further, the semiconductor pillar layer is connected with positive and negative electrodes; the hot side and the transparent crystal cold side are connected to opposite ends of the semiconductor pillar layer respectively; the transparent crystal cold side covers an entire surface of the semiconductor pillar layer and provides a working surface; a thickness of the transparent crystal cold side is not less than 1 mm; the hot side of the Peltier cooler is composed of a ceramic substrate to form a ceramic hot side; the ceramic substrate and the metal conductors of the semiconductor pillar layer are fixedly connected; the semiconductor pillar layer is set between the hot side of the and the transparent crystal cold side.

Further, the one or more sets of semiconductor pillar layers each connecting one hot side are arranged on one side, opposite two sides or multiple sides of the transparent crystal; or, the semiconductor pillar layer is annular, and electronic components are arranged in an annular region; the hot side is annular, and is fixed with one side of the semiconductor pillar layer; the transparent crystal cold side is fixed with the other side of the semiconductor pillar layer; a hollow region of the semiconductor pillar layer, a hollow region of the hot side, and together with the transparent crystal region forms the light-transmitting region.

Further, the hot side of the Peltier cooler is connected to the heat dissipation assembly, so as to transferred heat from the hot side of the Peltier cooler to the heat dissipation assembly for heat dissipation.

Further, the heat dissipation assembly comprises a heat pipe and a heatsink connected to the heat pipe; the heat pipe is able to transfer heat from the hot side to the heatsink for heat dissipation; the heat pipe directly contacts the hot side or connects the hot side through a thermally conductive member; the heat pipe is installed on or inserted in the heatsink.

Further, one end of the thermally conductive member or the heat pipe is adapted for and contacts with the hot side of the Peltier cooler; the heat pipe forms a ring, and the thermally conductive member is fitted in the ring; there is a refrigerant inside the heat pipe; the heatsink is one or more of: a plate fin heatsink, plate fins, or thermally conductive plates.

The advantages of the present invention are:

The hair removal device of the present invention has a transparent crystal to cool the head surface, and provide an ice cooling effect for the user with a comfortable experience.

Further, the Peltier cooler of the present invention uses a transparent crystal as a cool side of to replace a ceramic plaque, and the transparent crystal is directly fixedly connected with p & n-type semiconductor pillars so that a new type of Peltier cooler is obtained. At the same time, the transparent crystal can directly contact with skin and form the head surface to remove hair. Use the transparent crystal directly as a cool side of the Peltier cooler and to form a depilation surface, which can obtain the following advantages:

1) cooling rate and efficiency are improved since a middle layer of traditional Peltier cooler is eliminated, and the loss of cooling rate is reduced;

2) the whole front surface of the transparent crystal is in contact with the skin or the contact surface, which increases the cooling area and provides a better experience; and 3) Using the transparent crystal as the cold side, the pulsed light irradiates the skin through the transparent crystal, and is cooled by the transparent crystal, thereby pain or discomfort caused by light is greatly reduced or eliminated.

The present invention will be described in further detail below in conjunction with accompanying drawing.

DETAILED DESCRIPTION OF THE INVENTION

Figure 1:
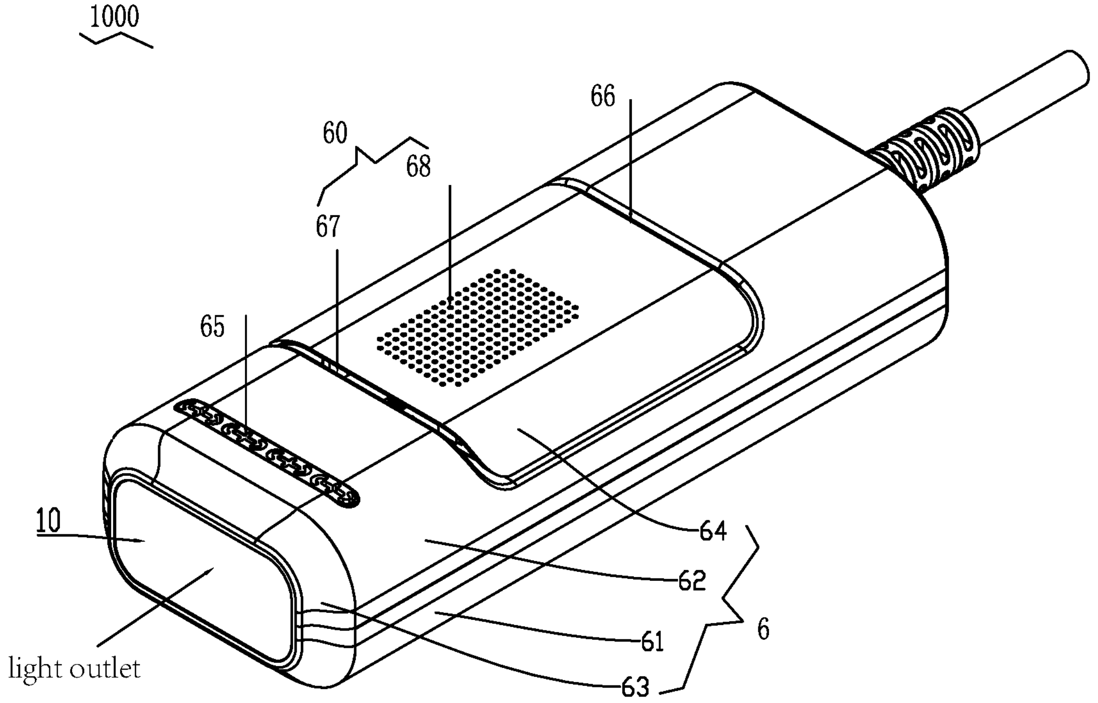
FIG. 1 is a perspective view of a hair removal device in accordance with a first embodiment of the present invention.
Figure 2:
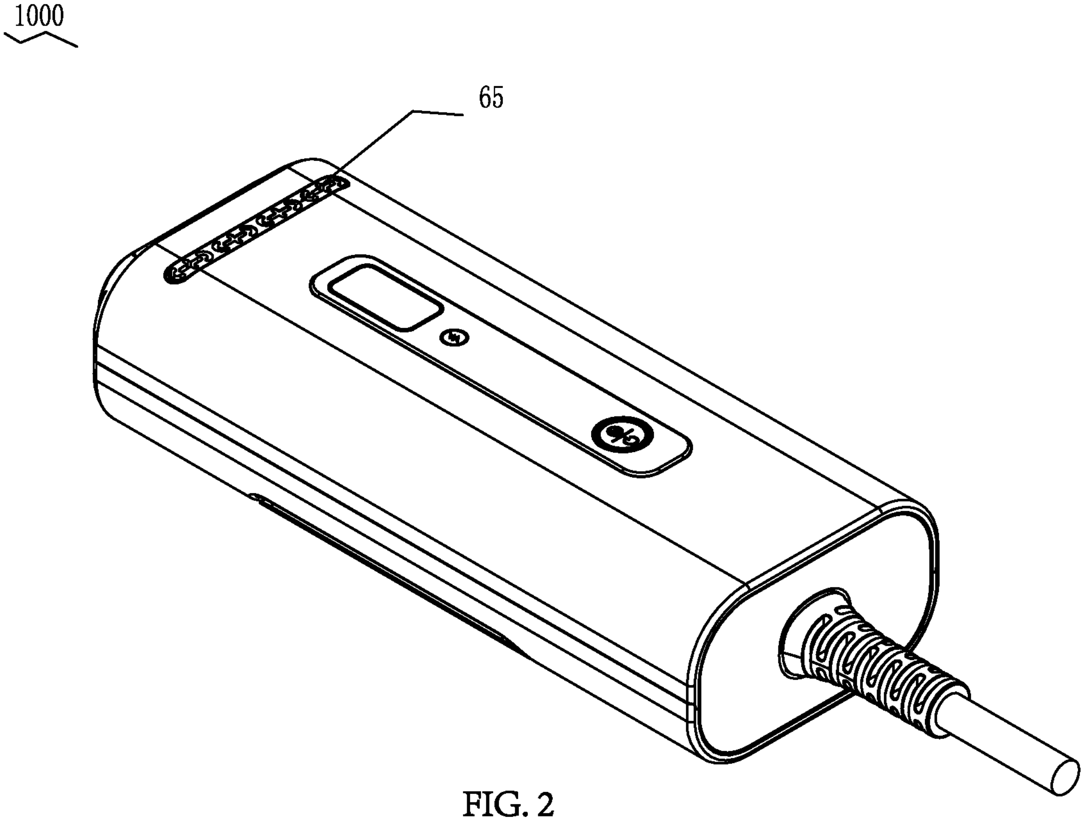
FIG. 2 is another perspective view of the hair removal device in accordance with the first embodiment of the present invention.

It should be noted that, in the case of no conflict, each embodiment in the present invention and the features in the embodiments can be combined with each other, and the present invention will be described in further detail below in conjunction with the accompanying drawings and specific embodiments.

First Embodiment of the Hair Removal Device

Referring to FIGS. 1-7, the present invention provides a hair removal device 1000, which comprises a head for hair removal, heat dissipation assembly 2, light source assembly 3, power supply unit 4 and control circuit board 5. The heat dissipation assembly 2, the light source assembly 3, the power supply unit 4 and the control circuit board 5 are installed in a housing 6 of the hair removal device. The control circuit board 5 is electrically connected with the light source assembly 3 and the power supply unit 4 to control the light source to emit pulsed light for hair removal. The power supply unit 4 can supply power to the light source assembly 3. The head of the hair removal device 1000 is equipped with a Peltier cooler which provides a surface for hair removal. The control circuit board 5 controls the power supply unit 4 to excite the light source assembly 3 to emit pulsed light, and the pulse light transmits the surface for hair removal treatment. The heat dissipation assembly 2 is connected to the Peltier cooler 1 for heat dissipation. The housing 6 is provided with first air inlets 60 and an air outlet 66. The hair removal device 1000 can also be provided with a power cord and/or a charging interface to be connected to an external power source.

The heat dissipation assembly 2 is mainly used for heat dissipation of the Peltier cooler 1, and includes heat pipes 21, a heatsink 23 connected to heat pipes, and a fan 25. The heat pipes 21 are connected to the Peltier cooler 1, so as to transfer heat generated by the Peltier cooler 1 to the heat dissipation assembly 2 for heat dissipation. The fan 25 is installed in a cavity 28, one side of the cavity 28 extends to form an air outlet channel 280, and the end of the air outlet channel 280 is connected to the air outlet 66.

The first air inlets 60, heat dissipation air paths of the heatsink, the fan 25, the air outlet channel 280, and the air outlet 66 communicate with each other to form a heat dissipation air path (as shown as the arrow in FIG. 4) for the heatsink, that is, the first heat dissipation air path. The fan starts, cold air enters through the first air inlet 60 to the heatsink 23 to take away heat, is discharged from the fan 25 through the air outlet channel 280 and the air outlet 66 to outside so as for air cooling of the heatsink. The fan 25 is electrically connected with is controlled by the control circuit board 5.

The cooler 1 installed on the head for hair removal can adopt the cooler in the prior art which provides a work surface for hair removal, and the work surface is cooled by the heat dissipation assembly 2. In some embodiments, the cooler 1 installed in the head for hair removal is a Peltier cooler, and the Peltier cooler is used to cool the working surface so as to obtain a cooling working surface. In a preferred embodiment, the cold side of the Peltier cooler 1 installed in the head of the hair removal device is used as the working surface. The Peltier cooler 1 adopts a transparent crystal directly as cold side 10 and as the working surface for contacting skin, specifically refer to the following description. The heat pipe 21 is connected to the hot side 12 of the Peltier cooler 1, so as to transfer heat from the hot side 12 of the Peltier cooler 1 to the heat dissipation assembly 2 for heat dissipation.

The housing 6 includes an upper housing 61 and a lower housing 62 (the upper and lower positions are relative, here is only for convenience of description), and also includes a head housing 63. In the first embodiment of the hair removal device, the upper housing 61 and/or the lower housing 62 are provided with second air inlets 65 corresponding to the light source assembly 3. Preferably, both the upper and lower housings are provided with second air inlets 65. The second air inlets 65 communicate with an air path of the light source assembly 3, and is used for cold air to enter to the light source assembly 3 for dissipate heat.

The lower housing 62 is provided with an opening 69, and the heatsink 23 is located behind the opening. The outer cover of the opening 69 is provided with a cover 64, and the cover 64 is fastened to the opening 69 of the lower housing. Air holes 68 are provided in the baffle, and the air holes 68 may be one or more groups of through holes densely arranged. The air holes 68 are used to communicate the external environment with the air path inside the casing, specifically, the air path of the heatsink, so that cold air enter from the air holes to the heatsink 23 for air cooling and heat dissipation.

Figure 7:
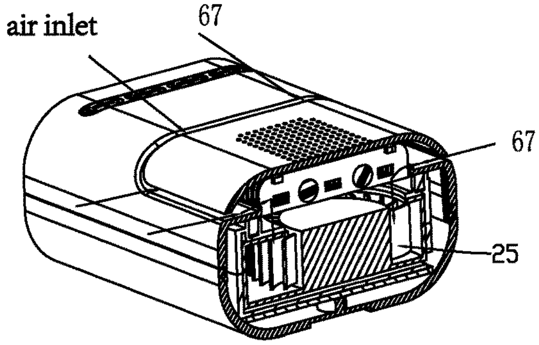
FIG. 7 is the sectional view of the hair removal device and air ducts of the heatsink in accordance with the first embodiment of the present invention.
Figure 8:
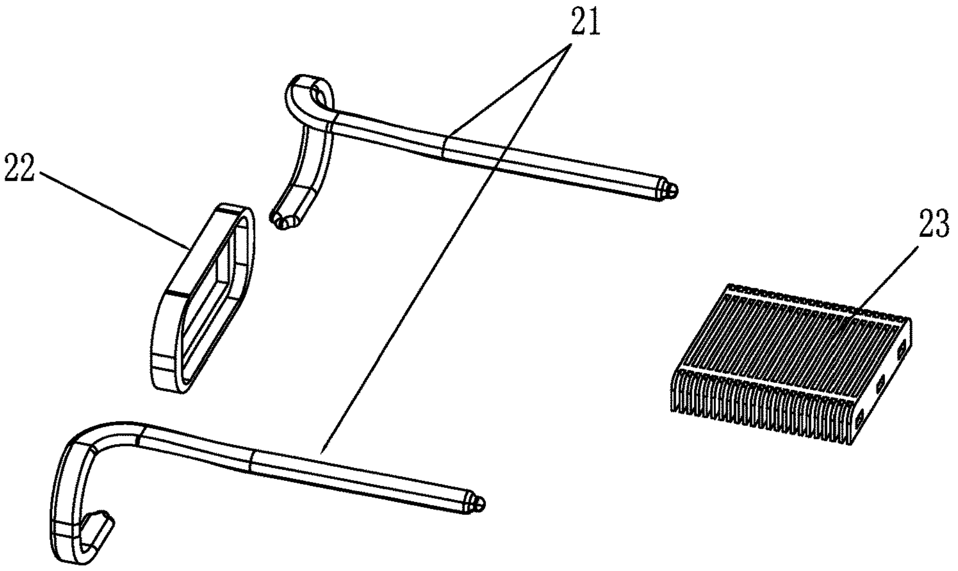
FIG. 8 is an exploded view of the heat dissipation assembly of a Peltier cooler in accordance with the first embodiment of the present invention.
Figure 9:
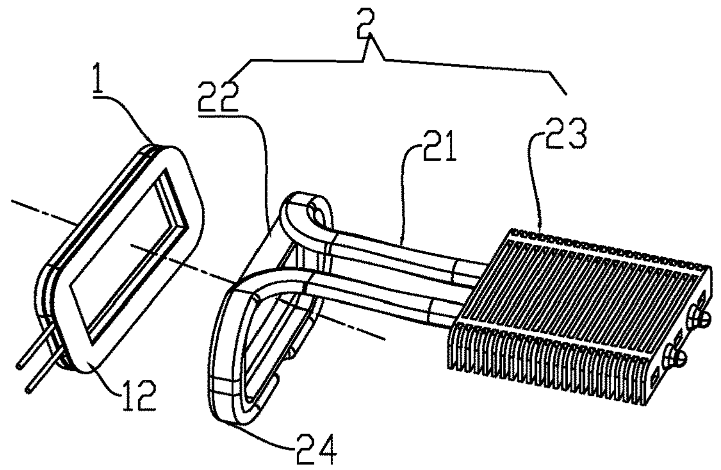
FIG. 9 is the schematic diagram of heat dissipation system of the Peltier cooler in accordance with the first embodiment of the present invention.
Figure 10:
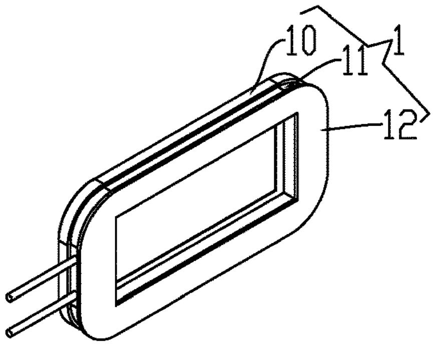
FIG. 10 is a perspective view of the Peltier cooler in accordance with the first embodiment of the present invention.
Figure 11:
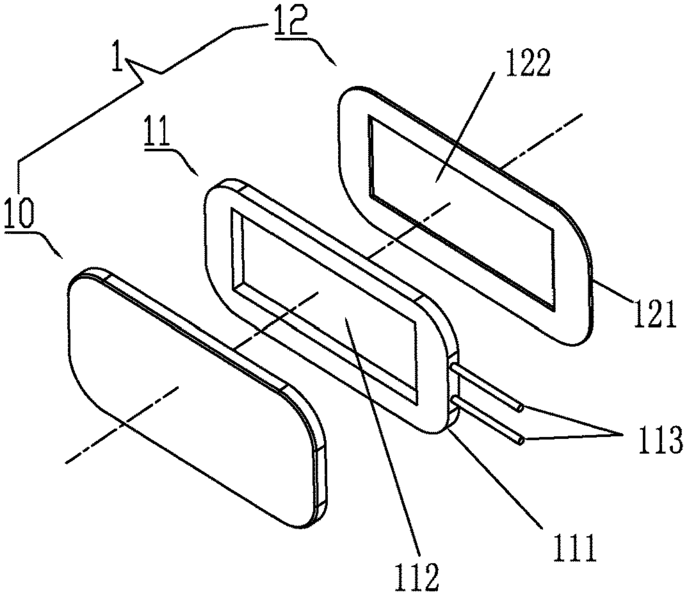
FIG. 11 is an exploded view of the Peltier cooler in accordance with the first embodiment of the present invention.

A gap between the edge of the cover 64 and the edge of the opening 69 of the lower housing is used as an air outlet 66 and a side air inlet 67, the air outlet 66 communicates the air outlet channel 280, and the side air inlet 67 is used for air cooling the heatsink. Referring to FIGS. 1 and 7, the gap is formed between the cover 64 and the peripheral edge of the opening 69 of the lower housing 62, wherein the gap at one side forms the air outlet 66, and the gap at the other sides forms the side air inlet 67. The side air inlet 67 communicate with air ducts of the heatsink 23 behind the lower housing 62 so that air enters from side to the heatsink 23 to increase the amount and speed of cold air, which can reduce water mist or water droplets to damage the control circuit board 5 due to air entering from front. The air holes 68 in the housing are used for air entering forward, and the side air inlet 67 is used for air entering from sides, thereby air enters in multi-directions from the first air inlets 60 to cool the heatsink, which can improve heat dissipation efficiency. The first air inlet 60 is used to introduce air to the surface of the heatsink, and preferably includes a side air inlet 67 formed by the gap between the cover 64 and the edge of the opening in lower housing, and also includes one or more groups of holes 68 in the cover. In other embodiments, the first air inlet 60 is not limited to the side air inlet 67 or the air holes 68.

The upper housing 61 is equipped with keys or key pads. The control circuit board 5 is installed behind the upper housing 61.

The light source assembly 3 includes a light source 31 and a reflector 32 provided outside the light source. When the light source 31 is energized, pulsed light is generated, and the control circuit board 5 controls the power supply unit 4 to excite the light source. The pulsed light is emitted from the light source assembly and transmitted to the head for hair removal to the skin surface, thereby performing hair removal. In this embodiment, heat generated by the light source assembly 3 is also dissipated through the heat dissipation assembly 2. The reflector 32 is made of heat-conducting material, and heat generated by the light source 31 is conducted to the reflector 32 for heat dissipation. Light source 31 can adopt lamp tube. The power supply unit 4 may be a capacitor battery or a power conversion module.

In the first embodiment of the present invention, the light source assembly 3 is installed in the light source frame 7, the light source frame 7 is installed in the housing 6 and is positioned in the head, a reflective cover 71 is used to connect the head and the light source frame 7, the pulsed light emitted from the light source assembly 3 is transmitted to the head through the reflective cover 71. Both ends of the light source assembly 3 are installed in the light source frame 7, and a light shading cover 72 (FIG. 6) is provided in the light source frame 7 at each opposite end of the light source, and is used to guide air entering from the second air inlets 65 to the reflector for heat dissipation. The shading cover 72 is not only used to guide air, but also used to block the light to avoid light leakage at the two ends of the light source. The shading cover 72 can be in the shape of a plate, and the plate surface is inclined to the surface of the reflector 32. The shading cover 72 can also be a sealing sleeve, which is sleeved outside the ends of the light source.

In this embodiment, at least one ventilation passage 70 is arranged in the light source frame 7, and each ventilation passage 70 communicates the second air inlets 65 with a space around the light source assembly namely an air-cooling chamber 33. The ventilation passage 70 communicates the second air inlets 65 in the housing, and guides air entering from the second air inlets 65 to the light source assembly for heat dissipation. Preferably, at least one ventilation passage 70 is respectively provided in the upper and lower parts of the light source frame 7, and correspondingly, the upper and lower housings 61, 62 are provided with second air inlets 65 connected to the ventilation passage 70.

The light source assembly 3 and the reflective cover 71 are installed in the light source frame 7, and gaskets 73 are respectively set on the outer periphery of the light source assembly 3 and the reflective cover 71 for fixing and preventing light leakage.

In this embodiment, the light source assembly 3 connects an air guide cover 30, and a space between the air guide cover 30 and the light source assembly 3 forms an air-cooling chamber 33 for heat dissipation of the light source assembly. The air-cooling chamber 33 corresponds to the space out of the light source assembly. The air-cooling chamber 33 is in air communication with the ventilation passage 70 defined in the light source frame 7, and further in air communication with the second air inlets 65 in the housing 6. The airflow path between the air-cooling chamber 33 and the cavity of the fan is connected. The air-cooling chamber 33 surrounds the light source assembly 3. Specifically, the reflector 32 of the light source is located at one side of the air guide cover 30, and the air-cooling chamber 33 is defined between the air guide cover 30 and the reflector 32 of the light source, and air enters into the air-cooling chamber is used for reflector 32 for heat dissipation. The air guide cover 30 has shape and size corresponding to the reflector 32 of the light source and is installed beside the reflector to define the air-cooling chamber 33. The air guide cover is configured to reduce a height thereof and maximize a surface area thereof, so as to form a negative pressure in the air-cooling chamber 33 when the fan is started for increasing air flow from the second air inlets 65. Preferably, one side of the air guide cover 30 covering the reflector 32 is trumpet-shaped, and the other side thereof is configured with a hollow connection end 34. The trumpet-shaped side is clamped and installed on the light source frame 7. The hollow connecting end 34 communicates the air-cooling chamber 33 and the air path of the fan 25. The hollow connecting end 34 is designed to maximize to air flow.

The second air inlets 65 in the housing 6, the space out of the light source assembly, that is, the air-cooling chamber 33, the cavity 28 for installing the fan, the air outlet channel 280, and the air outlet 66 communicate with each other to form a heat dissipation air path of the light source assembly 3, namely a second air cooling path. When the fan 25 starts, environmental air enter through the second air inlets 65 to the light source assembly, and heat is taken away from light source assembly by air. The hot air enters the cavity 28 and discharged to the air outlet channel 280 by the fan, and finally is discharged through the air outlet 66 to outside, so as to perform air cooling and heat dissipation for the light source assembly 3.

The air guide cover 30 is connected with a sealing member 8. One side of the sealing member 8 is provided with an air guide connecting pipe 81; one end of the connecting pipe 81 is connected to the hollow connecting end 34 of the air guide cover 30 so as to communicate with the air-cooling chamber 33; the other end of the connecting pipe 81 is connected to the fan 25. An annular sealing ring 82 is set at the other side of the sealing member 8, and the annular sealing ring 82 is installed around the air inlet opening of the fan 25 to prevent air leakage. Another annular sealing ring 83 is further provided to connect the annular sealing ring 82 of the sealing member 8. The other annular sealing ring 83 is installed on the air outlet channel 280 of the cavity 28 to prevent air leakage.

In this embodiment, the fan 25 is installed inside the cavity 28, and the cavity 28 includes an annular wall, which is fastened with a cover 29 to fix the fan 25 in the cavity. One side of the cavity 28 extends toward the air outlet 66 to form an inclined air outlet channel 280 which is able to prevent air from flowing backward. The air path between the air outlet 250 of the fan, the air outlet channel 280 and the air outlet 66 is in air communication. A center opening of the cover 29 is aligned with the top or bottom opening of the fan, and together form the air inlet of the fan. The annular sealing ring 83 of the sealing member is installed on the opening of the cover 29 to prevent air leakage.

First Embodiment of Peltier Cooler

With reference to FIGS. 8-14 together, the Peltier cooler 1 provided in the first embodiment of the present invention, is installed in the head of the hair removal device, and provide a hair removal surface to contact with skin. Wherein, the Peltier cooler 1 adopts a transparent crystal directly as the cold side 10 and as the hair removal surface to contact with skin. The heat pipes 21 of the heat dissipation assembly 2 is connected to the hot side 12 of the Peltier cooler 1, and transfers heat from the hot side 12 of the Peltier cooler 1 to the heat dissipation assembly 2 for heat dissipation. Peltier cooler 1 is fixed in head housing 63. The head housing 63 is tightly assembled at front ends of the upper and lower housings 61, 62, and is tightly fixed with the light source frame 7. The head can be further fixed by fasteners such as screws, positioning columns or buckle structures. The head housing 63 is assembled with the upper and lower housings 61, 62 and the light source frame 7.

The Peltier cooler 1 is electrically connected with the control circuit board 5. The control circuit board 5 controls the light source assembly 3 to emit pulsed light that transmits the Peltier cooler 1 for hair removal. The control circuit board 5 can also be used to control the Peltier cooler 1 to work. It can be understood that the Peltier cooler 1 can also be provided with an independent power supply or an independent control circuit board to individually control the Peltier cooler 1 to work.

One end of heat pipes 21 connect a thermally conductive member 22. The thermally conductive member 22 connects the hot side 12 of Peltier cooler 1, is used for transfer heat of the hot side 12 of the Peltier cooler to heat pipes 21 through the thermally conductive member 22 for heat dissipation by heat pipes 21 and the heatsink 23. The heatsink 23 is a plate fin heatsink.

The thermally conductive member 22 is generally a metal member, preferably copper, and the shape of thermally conductive member 22 is adapted to the shape of the hot side 12 of the Peltier cooler 1, and is in contact with the hot side 12 of the Peltier cooler 1 for rapid heat transfer. There is refrigerant filled in the heat pipes 21, and the heat pipes are fixed on the surface or inside of the plate fin heatsink 23. The heat pipes 21 are preferably copper pipes. One end or a section of heat pipes 21 connected to the Peltier cooler 1 form a ring 24, which is adapted to the shape and size of the hot side of the Peltier cooler 1. The thermally conductive member 22 has a contour corresponding to the ring 24 of heat pipes 21, and the thermally conductive member 22 and the ring 24 of heat pipes 21 are sleeved and attached to each other. The heat conducting member 22 and the ring 24 of heat pipes can be soldered to form a ring fit, so that heat can be quickly transferred to heat pipes 21. In this embodiment, the heat conducting member 22 is a metal ring. Heat is transferred from the hot side to the ring 24 of heat pipes 21, and the refrigerant in the heat pipes absorbs heat and evaporates, and is cooled to be condensed by the heatsink so as to transfer heat to the heatsink.

The fan 25 of the heat dissipation assembly cooperates with the fin heatsink 23 for heat dissipation. The heatsink 23 and fan 25 are arranged up and down, and the air paths communicate. The fin heatsink 23 is installed inside the housing 6 and behind the cover 64 of the lower housing. The air holes 68 in the cover 64 and the side air inlet 67 communicate with air ducts of the heatsink 23. The air duct of the heatsink communicates with the air path of the fan 25, so that the hot air in the ducks of the heatsink flows to the fan, and discharged by the fan to the air outlet channel 280 and then discharged from the air outlet 66 to outside. The fin heatsink 23 is installed at one side of the air inlet of the fan 25.

In the present embodiment, the fan 25 and the cavity 28 are used for heat dissipation for the light source assembly 3 and the heatsink 23 of the Peltier cooler. Specifically, the fan 25 is started, and the ambient cold air is drawn from the second air inlets 65 and the first air inlet 60 (that is, the side air inlet 67/air holes 68), and the cold air from the second air inlets 65 enters into the air-cooling chamber 33 of the light source assembly to transfer heat of the light source assembly, and flows to the fan 25. The cold air from the air inlet 67/air holes 68 transfer heat from the heatsink 23 and then flows to the fan 25. Finally, the fan 25 discharges the hot air from the air outlet 66 after the air channel 280 to the external environment, and perform heat dissipation for the light source assembly 3 and the heatsink 23, and the heatsink 23 dissipates heat and cools heat pipes, thereby performing cooling the Peltier cooler 1.

The Peltier cooler 1 of this embodiment of the present invention comprises a cold side 10, a semiconductor pillar layer 11 with metal conductors, and a hot side 12. The semiconductor pillar layer 11 is located between the cold side 10 and the hot side 12. Wherein, the cold side 10 of the Peltier cooler is made of transparent crystal, thereby forming a transparent crystal cold side; the inner surface of the cold side 10 is fixedly connected with the metal conductors of the semiconductor pillar layer 11. The hot side 12 of the Peltier cooler is a ceramic substrate, and the inner surface of the hot side is fixedly connected with the metal conductors of the semiconductor pillar layer 11. The ceramic hot side 12 and the transparent crystal cold side 10 sandwich the semiconductor pillar layer 11 therein to form the Peltier cooler 1. The ends of the semiconductor pillar layer 11 are connected with positive and negative electrodes 113. The transparent crystal can be transparent materials with high light transmission, high thermal conductivity, and high heat resistance, such as natural crystals or diamonds.

The semiconductor pillar layer 11 is fixedly connected between the transparent crystal cold side 10 and the ceramic hot side 12, which can be obtained using methods in the prior art. For example, the inner surfaces of the transparent crystal cold side 10 and the ceramic hot side 12 are firstly metallized, and then welded to the metal conductors of the semiconductor pillar layer 11 to form a soldering fixation. Alternatively, the semiconductor pillar layer 11 is bonded to the crystal cold side 10 and the ceramic hot side 12 by thermally conductive adhesive to form a bonding fixation.

In this embodiment, the semiconductor pillar layer 11 is annular, which has an annular region 111 used for arranging electronic components, and a hollow region 112 is for light transmitting. The semiconductor pillar layer 11 are formed by p & n-type semiconductor pillars with metal conductors to form circuit. Using the Peltier effect of the semiconductors, when the direct current passes through the p & n-type semiconductor pillars placed in series, there will cause a temperature difference between two sides, heat will be transported from one side to the other. The heat is transported from the transparent crystal cold side 10 to the ceramic hot side 12 of the Peltier cooler. Of course, other suitable materials instead of ceramic can also be used to make the hot side.

The shape and size of the ceramic hot side 12 are adapted to the semiconductor pillar layer 11, for example, it is also annular, which has an annular region 121 as a heat dissipation surface, and a hollow region 122 for light transmitting. The annular shape of the ceramic hot side 12 fits with the annular shape of the semiconductor pillar layer 11 for rapid heat dissipation. The hollow regions of the ceramic hot side 12 and the semiconductor pillar layer 11 are aligned and communicated.

The transparent crystal cold side 10 covers the entire surface of the semiconductor pillar layer 11, and forms a cold side. The transparent crystal cold side 10 is a whole piece or a whole crystal with a continuous surface. Preferably, the thickness of the transparent crystal cold side is not less than 1 mm, so as to improve the strength of the Peltier cooler 1, reduce the damage risk of assembly, and prolong the service life. The transparent crystal material of this embodiment has high light transmittance and high thermal conductivity, so that the pulsed light can transmit the transparent crystal for hair removal operation, and the high thermal conductivity is beneficial to improve the cooling efficiency and effect.

The transparent crystal cold side 10 has a light-transmitting region 102, and a peripheral annular region 101 fitfully bonded to the semiconductor pillar layer 11. Correspondingly, the light-transmitting region 102 of the transparent crystal cold side covers on the hollow region 112 of the semiconductor pillar layer 11, so that the hollow region is covered and allows light to transmit through. The entire cooling area of the transparent crystal cold side 10 includes a transparent region 102 and an annular region 101 around the transparent region. The entire surface of the crystal is cooled, which increases the cooling area and provides a better experience.

Figure 12:
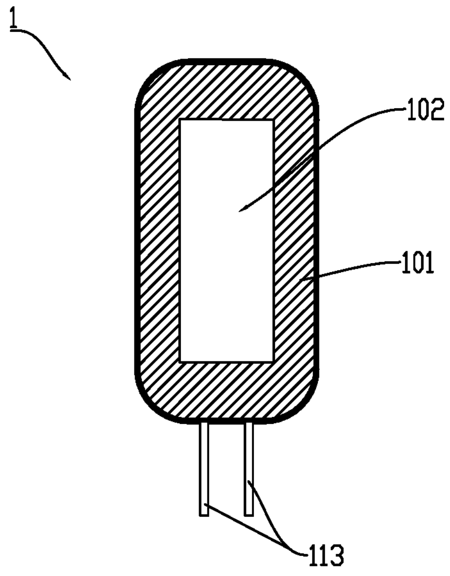
FIG. 12 is a front view of the Peltier cooler in accordance with the first embodiment of the present invention.
Figure 13:
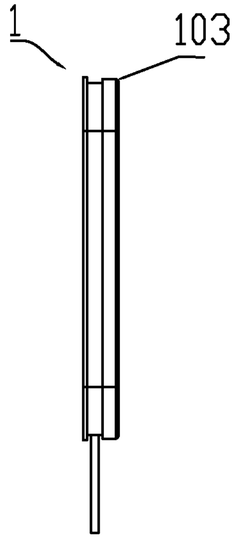
FIG. 13 is a side view of the Peltier cooler in accordance with the first embodiment of the present invention.
Figure 14:
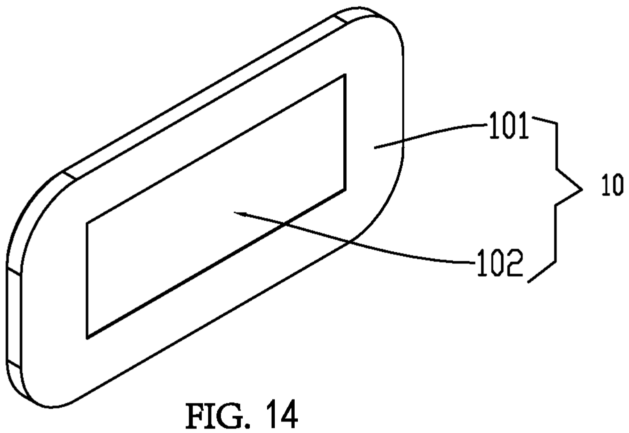
FIG. 14 is a perspective view of the Peltier cooler for showing a cold side thereof in accordance with the first embodiment of the present invention.

Referring to FIG. 12, the annular region 101 of the transparent crystal cold side 10 forms an annular shading region (the shaded part in FIG. 12) after light-shielding treatment, which is used to shield the internal electronic components. Specifically, the light-shielding treatment can be performed by coating a light-shielding film on one or both sides of the transparent crystal, and then removing the light-shielding on the light-transmitting region; or, by printing a shielding layer directly on the annular region of the transparent crystal. The shading area is formed by surface treatment of the crystal cold side 10, which can be treated on both sides or any one side of the crystal, and can be treated by coating, spraying, printing or other methods.

The edges of the transparent crystal cold side 10 can be further processed to form an assembly position 103 (refer to FIG. 13), which is used for fixed assembly with an external housing (such as a head housing). In a more specific example, the assembly position 103 can be a beveled edge or a stepped surface, which can form a snap fit with the head housing 63.

Other Various Embodiments of Peltier Cooler

In other embodiments, the Peltier cooler 1 includes semiconductor pillar layers 11 and hot sides 12 and a cold side 10. The cold side 10 is made of transparent crystal to form a transparent crystal cold side. The surface of the transparent crystal is fixedly connected with one or more sets of the semiconductor pillar layers 11 and the hot sides 12 fixedly connected with the semiconductor pillar layers. The Peltier cooler has a light-transmitting region 102 provided by the transparent crystal.

Where the one or more sets of semiconductor pillar layers and the hot sides correspondingly fixed with semiconductor pillar layers are arranged at one side, opposite sides or multiple sides of the transparent crystal cold side.

Figure 15:
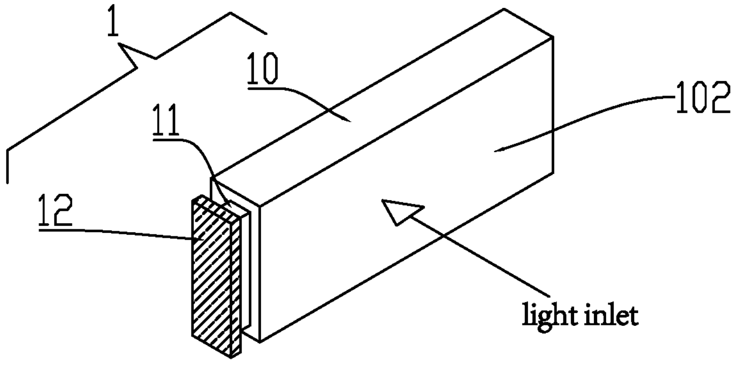
FIG. 15 is a perspective view of the Peltier cooler in accordance with a second embodiment of the present invention.

With reference to FIG. 15, the Peltier cooler 1 of the second embodiment of the present invention, the cold side 10 is a square (not limited to square) transparent crystal, one side of transparent crystal such as the left side is provided with a pair of semiconductor pillar layer 11 and hot side 12 fixedly connected with the semiconductor pillar layer. The semiconductor pillar layer 11 is provided with a pair of electrodes (not shown). The other two pairs of sides of the transparent crystal, such as the front and rear (or upper and lower) sides, can be used as the light-transmitting region 102 for the transmission of pulsed light for hair removal treatment. In a specific example, the hot side 12 of the Peltier cooler is made of a ceramic substrate to form a ceramic hot side. The inner surface of the ceramic substrate is fixedly connected with the metal conductors of the semiconductor pillar layer 11. The semiconductor pillar layer 11 is sandwiched between the ceramic hot side 12 and the crystal cold side 10. The hot side 12 and the transparent crystal cold side 10 are attached and fixed to opposite sides of the semiconductor pillar layer 11 respectively. The transparent crystal cold side 10 covers the entire surface of the semiconductor pillar layer 11 and provides a cold side.

Figure 16:
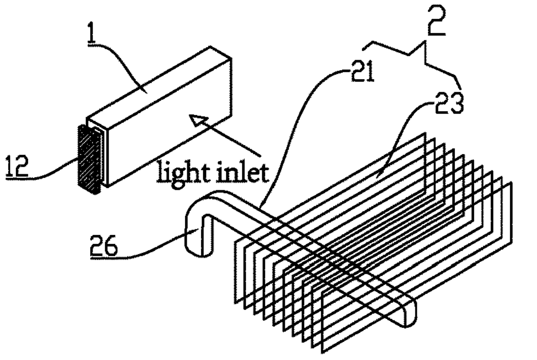
FIGS. 16(*a*)-16(*f*) illustrate the heat dissipation assembly of the Peltier cooler in accordance with the second embodiment of the present invention.
Figure 16:
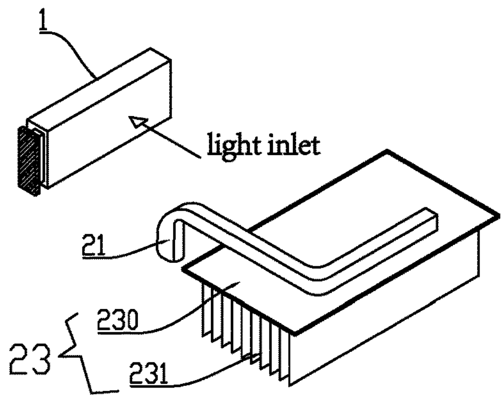
Figure 16:
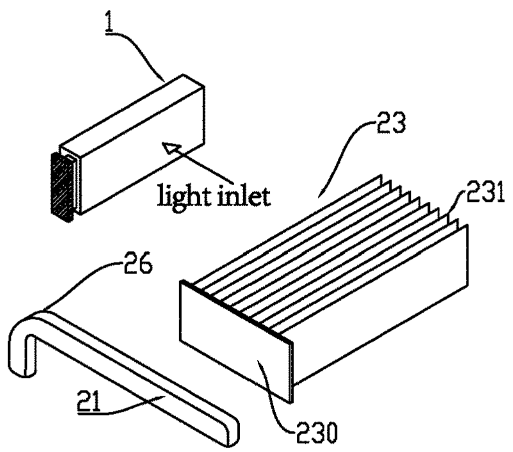
Figure 16:
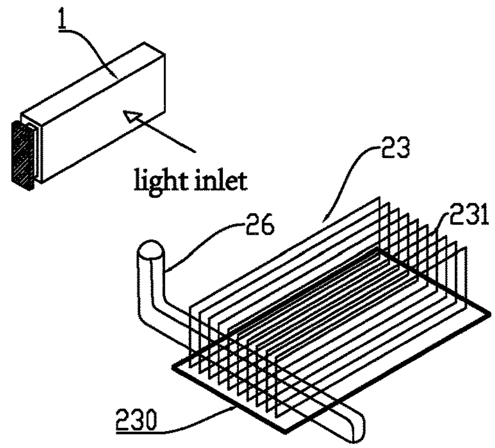
Figure 16:
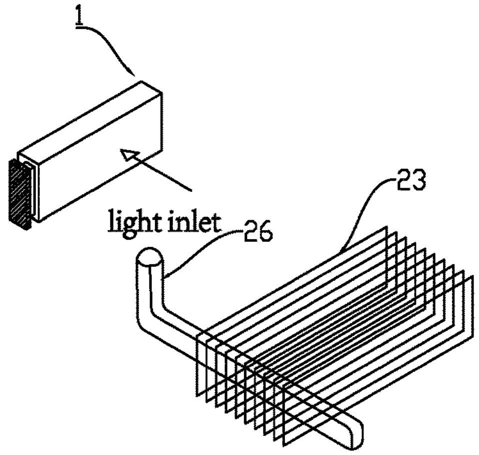
Figure 16:
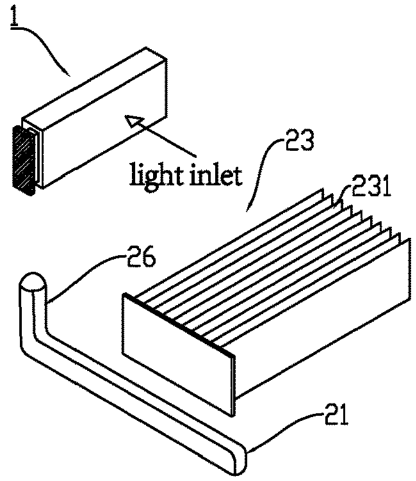

Further referring to FIGS. 16(*a*)-16(*f*), the Peltier cooler 1 of the second embodiment of the present invention is connected with the heat dissipation assembly 2, and heat of the Peltier cooler is transferred from the hot side 12 to the heat dissipation assembly for heat dissipation. The heat dissipation assembly 2 includes a heat pipe 21 and a heatsink 23 connected to heat pipe 21. The heat pipe is installed on the surface or inside of the heatsink. The heat pipe 21 is in direct contact with the hot side 12 of the Peltier cooler 1 or connect the hot side through a heat conducting member. In this embodiment, one end 26 of heat pipes are adapted to the shape of the hot side 12 of the Peltier cooler, and is in contact with each other; The end of the hot side 12 is bent, and the various bending shapes are shown in the figures, for example, L-shaped. The heat pipe 21 can be a capillary copper tube with circulating refrigerant filled inside. The heatsink is one or a combination of plate fin heatsinks, plate fins or thermally conductive plates. Various heatsink structures as shown in the figures, the heatsink 23 shown in FIG. 16(*a*) and FIG. 16(*e*), for example, includes one or more sets of plate fins arranged in parallel, and heat pipe 21 is inserted through and fixed in the parallel plate fins. FIGS. 16(*b*), 16 (*c*), 16 (*d*), and 16 (*f*), the heatsink 23 includes a thermally conductive base plate 230 and a group of parallel plate fins 231 fixed on one side of thermally conductive base plate 230. One end 26 of heat pipe 21 is bent and in contact with the hot side 12 of the Peltier cooler, and can be adapted for shape and size of the hot side 12. The heat pipe 21 is fixed on the other side of thermally conductive base plate 230, or inserted through one or more groups of parallel plate fins 231. The heatsink can be made of metal sheet with high thermal conductivity.

Figure 17:
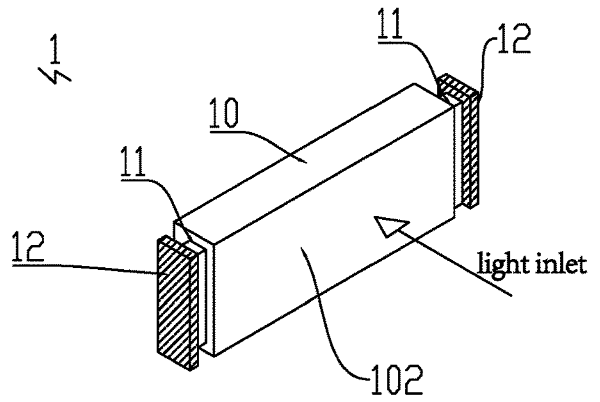
FIG. 17 is a perspective view of the Peltier cooler of in accordance with a third embodiment of the present invention.

Referring to FIG. 17, in the Peltier cooler 1 of the third embodiment of the present invention, the cold side 10 is a square (not limited to a square) transparent crystal, and two pair of semiconductor pillar layers and hot sides 12 each fixedly connected to one semiconductor pillar layer 11 are respectively arranged on the opposite sides of the transparent crystal such as the left and right sides. Each semiconductor pillar layer 11 is provided with a pair of electrodes (not shown). The other opposite sides of the transparent crystal, such as the front and rear sides (or the upper and lower surfaces), can be used as the light-transmitting region 102 for transmitting pulsed light for hair removal treatment. In a specific example, the hot sides 12 are made of ceramic substrates to form ceramic hot sides. The inner surface of each ceramic substrate is fixedly connected with the metal conductors of the corresponding semiconductor pillar layer 11. The semiconductor pillar layer 11 is sandwiched between the ceramic hot side 12 and the crystal cold side 10. The two hot sides 12 and the transparent crystal cold side 10 are attached and fixed to the opposite sides of the corresponding semiconductor pillar layer 11 respectively. The two sides of the transparent crystal cold side 10 respectively cover the entire surface of a corresponding semiconductor pillar layer 11 and provide a cold side.

Figure 18:
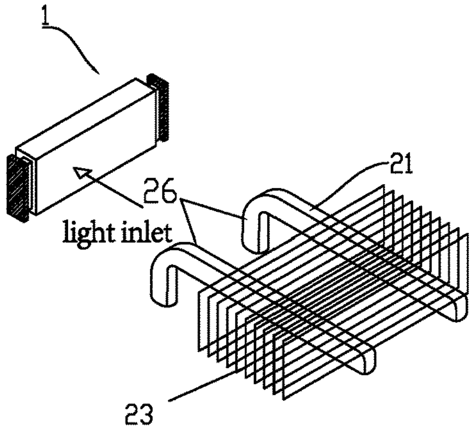
FIGS. 18(*a*)-18(*c*) illustrate the heat dissipation assembly of the Peltier cooler in accordance with the third embodiment of the present invention.
Figure 18:
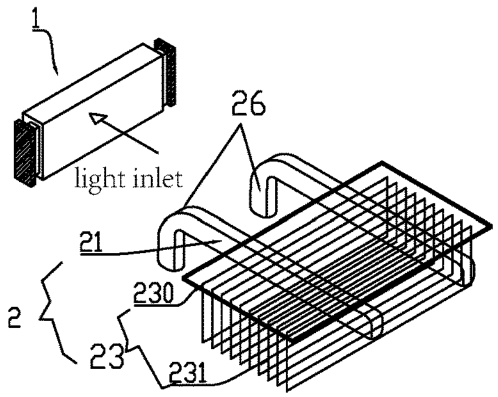
Figure 18:
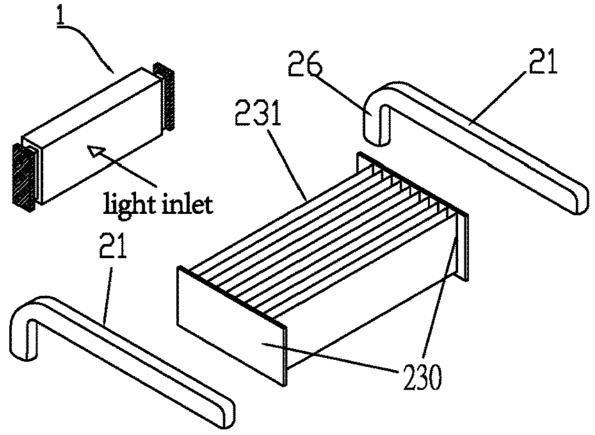

Referring further to FIGS. 18(*a*) to 18(*c*), in the third embodiment of the present invention, the Peltier cooler 1 is connected to the heat dissipation assembly 2, and heat of the Peltier cooler is transferred from the hot side 12 to the heat dissipation assembly for heat dissipation. In this embodiment, the heat dissipation assembly 2 includes two heat pipes 21 and a heatsink 23 connected to heat pipes 21. The heat pipes are installed on the surface or inside of the heatsink 23. The heat pipe 21 is in direct contact with the hot sides 12 of the Peltier cooler 1 or is in contact with the hot sides through a heat conducting member. For example, one end 26 of each heat pipe is adapted to the shape of the hot side 12 of the Peltier cooler, and is in contact with the hot side 12; The end of the heat pipe is bent, referring to the various bending designs shown in the figures, such as L-shape. The heat pipe 21 can be a capillary copper tube with circulating refrigerant inside. The heatsink is one or a combination of plate fin heatsinks, plate fins or thermally conductive plates. Among the various heatsink structures shown in the figures, the heatsink 23 shown in FIG. 18(*a*) includes one or more sets of plate fins arranged in parallel, and two heat pipes 21 are fixed to the one or more sets of parallel fins. In FIG. 18(*b*) and FIG. 18(*c*), the heatsink 23 includes a thermally conductive base plate 230 and one or more groups of parallel plate fins 231 fixed on one side of thermally conductive base plate 230. One end 26 of each heat pipe 21 is bent and in contact with one hot side 12 of the Peltier cooler, and the shape and size are adapted for the hot side 12. The heat pipes 21 are fixed on the other side of thermally conductive base plate 230 or inserted through or installed on a group of parallel plate fins 231. The heatsink can be made of metal sheets with high thermal conductivity. There can be provided with two thermally conductive base plate 230 each used to fix one heat pipe 21.

Figure 19:
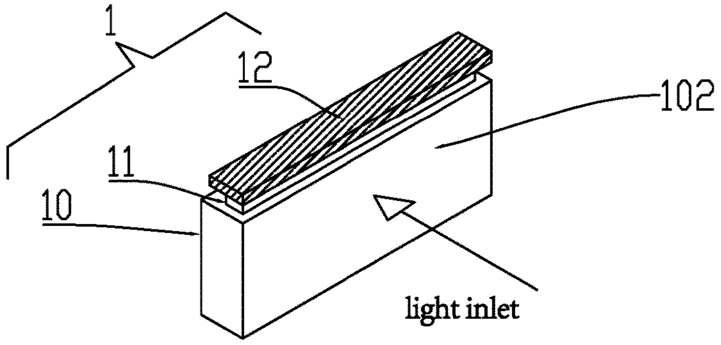
FIG. 19 is a perspective view of the Peltier cooler in accordance with a fourth embodiment of the present invention.
Figure 20A:
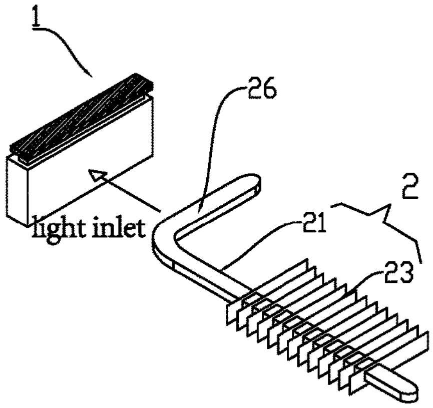
FIGS. 20(*a*)-20(*d*) illustrate the heat dissipation assembly of the Peltier cooler in accordance with the fourth embodiment of the present invention.
Figure 20C:
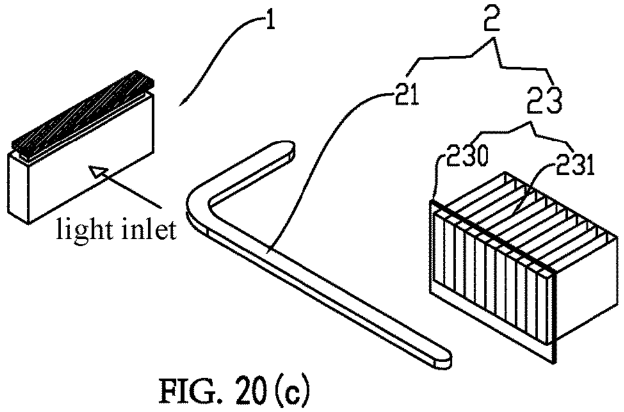
Figure 20B:
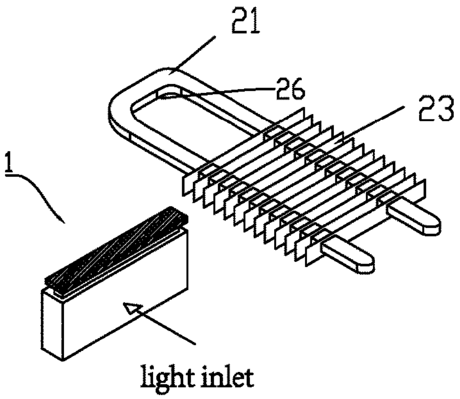
Figure 20D:
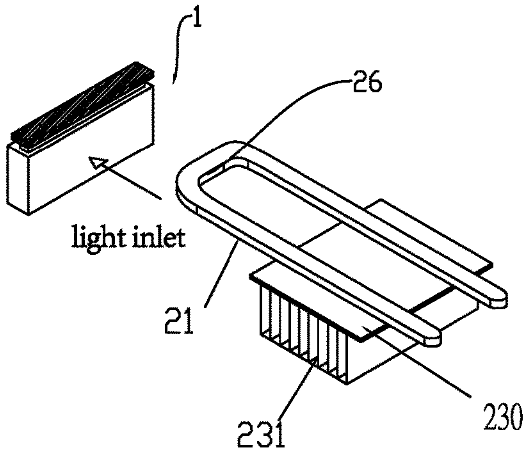

With reference to FIG. 19, in the Peltier cooler 1 of the fourth embodiment of the present invention, the cold side 10 is a square (not limited to square) transparent crystal, one side of transparent crystal such as the upper side is provided with a semiconductor pillar layer 11 with a hot side 12 fixedly connected thereon. The semiconductor pillar layer 11 is provided with a pair of electrodes (not shown). The other opposite sides of the transparent crystal, such as the front and rear (or left and right) sides, can be used as the light-transmitting region 102 for the transmission of pulsed light for hair removal treatment. In a specific example, the hot side 12 of the Peltier cooler is a ceramic hot side 12. The inner surface of the ceramic hot side 12 after metallization and the transparent crystal after metallization are welded with the metal conductors of the semiconductor pillar layer 11, so as to be respectively fixed on both ends of the semiconductor pillar layer 11. The transparent crystal cold side 10 covers the entire surface of the semiconductor pillar layer 11 and provides a cold side.

Further referring to FIGS. 20(*a*)~20(*d*), the Peltier cooler 1 of the fourth embodiment of the present invention is connected with the heat dissipation assembly 2, and heat of the Peltier cooler is transferred from the hot side 12 to the heat dissipation assembly for heat dissipation. The heat dissipation assembly 2 includes a heat pipe 21 and a heatsink 23 connected to heat pipe 21. Among the various heatsink structures shown in the figure, the heatsink 23 shown in FIG. 20(*a*) and FIG. 20(*b*) includes parallel plate fins, and heat pipe 21 is fixed on the parallel plate fins. In FIG. 20(*c*) and FIG. 20(*d*), the heatsink 23 includes a thermally conductive base plate 230 and parallel plate fins 231 fixed on one side of the thermally conductive base plate 230. One end 26 of heat pipe 21 is in contact with the hot side 12 of the Peltier cooler, and can be adapted for shape and size of the hot side 12. The heat pipe 21 is fixed on the other side of thermally conductive base plate 230, or is inserted through or installed on the parallel plate fins 231. The heat pipe 21 is bent into a U-shape or an L-shape, so as to obtain a close contact with the hot side 12.

Figure 21:
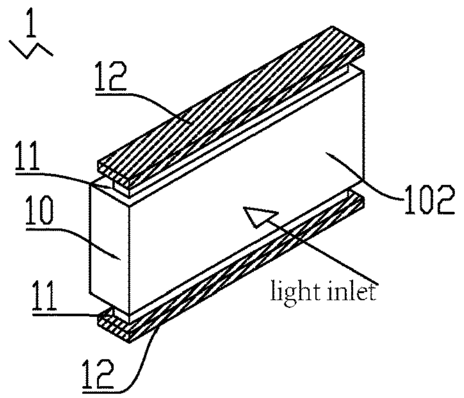
FIG. 21 is a perspective view of the Peltier cooler in accordance with a fifth embodiment of the present invention.
Figure 22A:
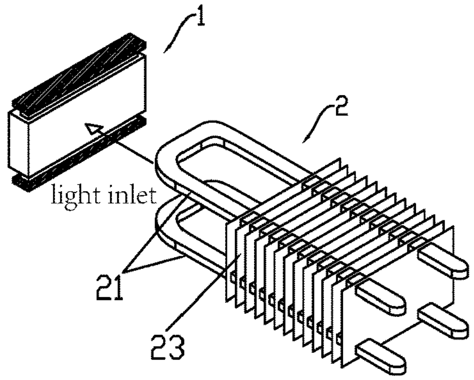
FIGS. 22(*a*)-22(*e*) illustrate the heat dissipation assembly of the Peltier cooler in accordance with the fifth embodiment of the present invention.
Figure 22B:
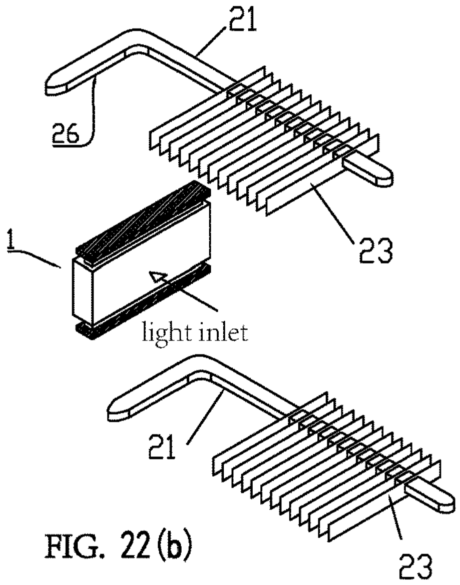
Figure 22C:
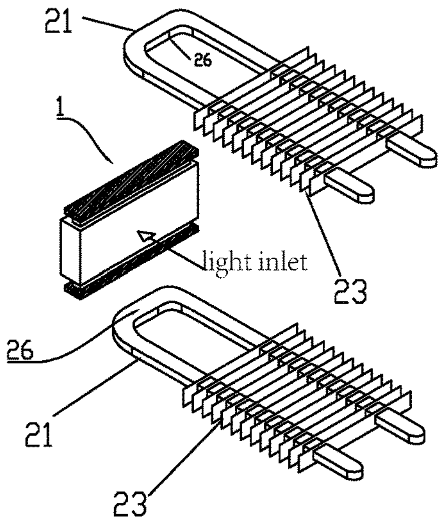
Figure 22D:
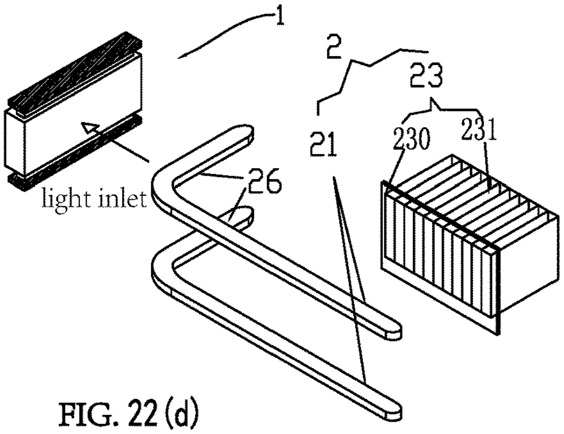
Figure 22E:
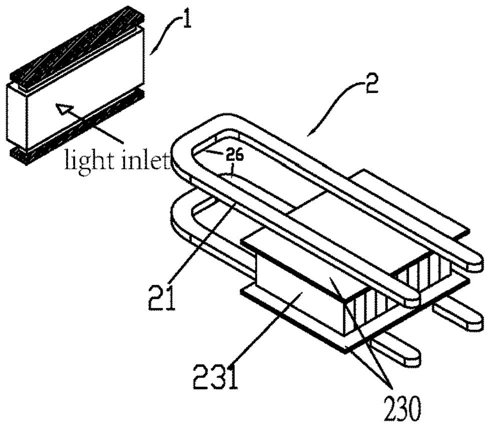

With reference to FIG. 21, in the Peltier cooler 1 of the fifth embodiment of the present invention, the cold side 10 is a square (not limited to square) transparent crystal, and the opposite sides of transparent crystal such as upper and lower sides are each provided with a semiconductor pillar layer 11 fixedly connected with one hot side 12. Each semiconductor pillar layer 11 is provided with a pair of electrodes (not shown). The other two opposite sides of the transparent crystal, such as the front and rear (or left and right) sides, can be used as the light-transmitting region 102 for the transmission of pulsed light for hair removal treatment. In a specific example, the hot sides 12 are ceramic hot sides, and the inner surface of each ceramic hot side is metallized and welded to the metal conductors of the corresponding semiconductor pillar layer 11. Each semiconductor pillar layer 11 is sandwiched between one ceramic hot side 12 and an upper side or a lower side of the transparent crystal cold side 10. The hot side 12 and the transparent crystal cold side 10 are attached and fixed to the opposite sides of the corresponding semiconductor pillar layer 11 respectively. The upper and lower sides of the transparent crystal respectively cover the corresponding semiconductor pillar layer 11 and the transparent crystal provides a cold side.

Further referring to FIGS. 22(*a*)~22(*e*), the Peltier cooler 1 of the fifth embodiment of the present invention is connected with the heat dissipation assembly 2, and heat of the Peltier cooler is transferred from the hot sides 12 to the heat dissipation assembly for heat dissipation. In this embodiment, the heat dissipation assembly 2 includes two heat pipes 21 and a heatsink 23 connected to heat pipes 21. The heat pipes are installed on the surface or inside of the heatsink. One end 26 of each heat pipes are in close contact with each hot side 12, and heat pipes 21 can be L-shaped or U-shaped or other suitable shapes to obtain a close contact with the hot side 12. Among the various heatsink structures shown in the figures, the heatsink 23 shown in FIG. 22(*a*), FIG. 22(*b*), and FIG. 22(*c*) includes one or more sets of parallel fins, and two heat pipes 21 are inserted and fixed in parallel plate fins. The heatsink 23 in FIG. 22(*d*) and FIG. 22(*e*) includes a thermally conductive base plate 230 and one or more sets of parallel plate fins 231 fixed on one side of thermally conductive base plate 230. One end 26 of each heat pipe 21 is bent and in contact with one hot side 12 of the Peltier cooler, and can be adapted for shape and size of the hot side 12. The heat pipe 21 is fixed on the other side of thermally conductive base plate 230 or inserted in the one or more sets of parallel plates 231.

Apply the Peltier cooler 1 and heat dissipation assembly 2 of the second to fifth embodiments (FIGS. 15 to 22(*e*)) in the hair removal device 1000 (FIGS. 1-7) of the foregoing embodiment, the Peltier cooler 1 installed in the head of the hair removal device, the transparent crystal cold side is used as the hair removal working surface. The heat dissipation assembly 2 is installed inside the housing 6. The heatsink 23 is installed below the fan 25, air ducts of the heatsink 23 communicate with the cavity 28, and the hot air from the heatsink 23 is discharged to the cavity 28 by the fan 25 and discharged to the outside from the air outlet 66. Refer to the foregoing embodiments for other structures of the hair removal device, and details are not repeated here.

In other embodiments, the hot side 12 of Peltier cooler 1 can also adopt other existing available materials instead of ceramic, for example, hot side 12 can be made from transparent materials to cover the semiconductor pillar layer 11.

Further, it can be understood that the transparent crystal cold side of Peltier cooler 1 can also be made from other transparent materials.

The Second Embodiment of the Hair Removal Device

With reference to FIGS. 23-26(*e*), the second embodiment of the hair removal device 1000 of the present invention, same as the first embodiment, includes a head for hair removal, a heat dissipation assembly 2, a light source assembly 3 and light source heat dissipation assembly, a power supply unit 4 and a control circuit board 5. The heat dissipation assembly 2, the light source assembly 3, the light source heat dissipation assembly, the power supply unit 4 and the control circuit board 5 are installed in the housing 6 of the hair removal device. The control circuit board 5 is electrically connected with the light source assembly 3 and the power supply unit 4 to control the light source to emit pulsed light for hair removal. The power supply unit 4 is used to supply power to the light source assembly 3. The head for hair removal of the hair removal device 1000 is equipped with a Peltier cooler to provide the hair removal work surface, and the control circuit board 5 controls the power supply unit 4 to excite the light source assembly 3 to emit pulsed light, and the pulse light transmits the hair removal work surface for hair removal treatment. The heat dissipation assembly 2 is connected to the Peltier cooler 1 for cooling. The housing 6 is provided with a first air inlet 60 and an air outlet 66. The hair removal device 1000 can also be provided with a power cord and/or a charging interface to be connected to an external power source.

The heat dissipation assembly 2 for the Peltier cooler 1 includes the heat pipe(s) 21, the heatsink 23 connected to heat pipes, and a fan 25. The heat pipe 21 is connected to the Peltier cooler 1, so as to transfer heat from the Peltier cooler 1 to the heat dissipation assembly 2 for heat dissipation. The fan 25 is installed inside or outside a cavity 28, the cavity 28 extends to form an air outlet channel 280, and the end of the air outlet channel 280 is connected to the air outlet 66. It can be understood that multiple and/or multi-directional air outlets can be provided to connect the air outlet channel 280, and correspondingly, air outlets 66 can be arranged on multiple sides of the housing 6 to form multiple or multi-directional air outlets accordingly.

The first air inlet 60, the air ducts of the heatsink, the fan 25, the air outlet channel 280, and the air outlet 66 are in air communication to form a heat dissipation air path (as the arrow in FIG. 4), that is, the first heat dissipation air path (for cooling the Peltier cooler). The fan starts, environmental air enters through the first air inlet 60 to the heatsink 23 for heat dissipation, flows to the fan 25 and is discharged by the fan 25 to the outside through the air outlet channel 280 and the air outlet 66 so as to perform heat dissipation for the Peltier cooler. The fan 25 is electrically connected with and controlled by the control circuit board 5.

The cold side of the Peltier cooler 1 of above-mentioned embodiments directly provides the hair removal surface of the head. Peltier cooler 1 adopts transparent crystal directly as cold side 10 and as the hair removal surface in contact with skin in use. The heat pipe 21 is connected to the hot side 12 of the Peltier cooler 1, so as to transfer heat from the hot side 12 of the Peltier cooler 1 to the heat dissipation assembly 2 for heat dissipation.

Different from the first embodiment of the hair removal device, in the present embodiments, the housing 6 is not necessary to define the second air inlets 65 for waterproof and dustproof.

The first air inlet 60, the air ducts of the heatsink, the fan 25, the air outlet channel 280, and the air outlet 66 are in air communication to form a heat dissipation air path (as the arrow in FIG. 4), that is, the first heat dissipation air path (for cooling the Peltier cooler). The fan starts, environmental air enters through the first air inlet 60 to the heatsink 23 for heat dissipation, flows to the fan 25 and is discharged by the fan 25 to the outside through the air outlet channel 280 and the air outlet 66 so as to perform heat dissipation for the Peltier cooler. The fan 25 is electrically connected with and controlled by the control circuit board 5.

The cold side of the Peltier cooler 1 of above-mentioned embodiments directly provides the hair removal surface of the head. Peltier cooler 1 adopts transparent crystal directly as cold side 10 and as the hair removal surface in contact with skin in use. The heat pipe 21 is connected to the hot side 12 of the Peltier cooler 1, so as to transfer heat from the hot side 12 of the Peltier cooler 1 to the heat dissipation assembly 2 for heat dissipation.

Different from the first embodiment of the hair removal device, in the present embodiments, the housing 6 is not necessary to define the second air inlets 65 for waterproof and dustproof.

As description in the first embodiment of the hair removal device, the first air inlet 60 and the air outlet 66 are arranged in the housing 6. The air outlet 66 in this embodiment can be provided in multiples or in multiple groups, and can be arranged in different positions or different directions in the housing 6, corresponding to the air flow direction in the fan 25, so as to form multi-directional air outlets and discharge heat in time.

Inside the housing 6, the heatsink 23 and the fan 25 can be installed up and down. Environmental air enters through the air inlet 60 in the housing 6 to the air ducts of the heatsink 23; where the top or the bottom of the cavity 28 (or fan housing) defines openings, so that air ducts of the heatsink 23 are connected with the air path of the fan 25; hot air enters the fan 25 from air ducts of the heatsink 23, is discharged by the fan 25 through the air outlet 250 at the side of the fan 25, the air outlet channel 280 and the air outlet 66 to outside. The air inlet 60 is preferably arranged in the housing 6 corresponding to the position of the heatsink 23 for the Peltier cooler and the heatsink 23' for the light source described below, so that the air can quickly flow to the heatsinks 23, 23' through the air inlet 60. The air inlet 60 can be one or one or more groups of holes or slots defines in the housing 6 (the upper housing 61 and/or the lower housing 62 and/or the cover 64), or it can be a gap between the edges of the cover 64 and the housing 6. There may also be multiple air outlets 66.

The light source assembly 3 includes a light source 31 and a reflector 32 provided out of the light source. When the light source 31 is energized, pulsed light is emitted, and the control circuit board 5 controls the power supply unit 4 to supply power to the light source. The pulsed light is emitted from the light source assembly and transmitted to the head for hair removal, thereby performing hair removal.

The heat from the light source assembly 3 is dissipated by the heat dissipation assembly for the light source assembly. The reflector 32 is made of heat-conducting material, and heat from the light source 31 is transferred to the reflector 32 for heat dissipation. Light source 31 can be a lamp tube. The power supply unit 4 may be a capacitor battery or a power conversion module. The light source 31 can be a lamp tube, and when the light source energized to emit lights which is reflected by the reflector 32, the temperature of the reflector 32 is high, so it is necessary for heat dissipation. The heat dissipation assembly for the light source assembly can cooperate with the heat dissipation assembly for the Peltier cooler. The reflector 32 has high thermal conductivity and good reflective effect.

A heat dissipation assembly for the light source assembly includes a heat pipe 21', a heatsink 23' and a fan 25 (shared with the fan in the heat dissipation assembly 2 for the Peltier cooler). The heat pipe 21' is connected between the light source assembly 3 and the heatsink 23', and transfers heat from the light source assembly 3 to the heatsink 23' for heat dissipation. The heatsink 23' is arranged in a heat dissipation air path which communicates the air inlet 60, the fan 25 and the air outlet 66; and the heatsink 23' is cooled through the heat dissipation air path.

Different from the first embodiment of the hair removal device, in this embodiment, the light source assembly 3 includes a thermally conductive cover 30', and the thermally conductive cover 30' is made of thermally conductive materials, is adapted for the shape of the reflector 32, and covers the back of the reflector 32. thermal grease can be pasted or coated between the reflector 32 and thermally conductive cover 30', so as to quickly transfer heat from the reflector 32 to thermally conductive cover 30'. One side of thermally conductive cover 30' is provided with a half cup-shaped (or trumpet-shaped) cover body 35, which fits and covers the back of the reflector 32, and the other side is provided with a tubular slot 34' for riveting/welding/attaching heat pipe 21'. The tubular slot 34' is (a copper tube or a capillary copper tube), transfers heat to heat pipe 21'. To facilitate assembly and fixation, thermally conductive cover 30' also includes a fixing plate 36, for example, the half cup-shaped (or trumpet-shaped) cover body 35 and a tubular slot 34' are located at opposite sides of the fixing plate 36. One end of heat pipe 21' is inserted in the tubular slot 34' of the thermally conductive cover 30', and contacts with each other, and thermal grease can be pasted or coated therebetween, so that heat from the reflector 32 is rapidly transferred through the thermally conductive cover 30' to the heat pipe 21'. There is refrigerant inside the heat pipe 21'. In this embodiment, heat pipe 21' is bent into a U shape or an L shape, and one end (or a section) 26 thereof is inserted into the tubular slot 34' of the thermally conductive cover 30', and riveted/welded/attached to the inner wall of the tubular slot 34'. The other end or both ends of the heat pipe 21' is equipped with a heatsink 23'. The refrigerant (liquid) inside heat pipe 21' (copper pipe) absorbed the heat and evaporate, flows in the heat pipe 21' due to the pressure inside the pipe for heat exchange, and the heat is transferred to the heatsink 23' (such as copper/aluminum sheet). The the heatsink 23' and the other end of the heat pipe 21' are set between the air outlet 250 of the fan 25 and the air outlet channel 280, or installed in the air outlet channel 280, so that air can take away heat from the heatsink 23'. Due to temperature difference, the refrigerant vapor in heat pipe 21' will condense into liquid again and flow to one end or a section 26 of heat pipe 21'. Such repeated circulation can dissipate heat from the reflector 32. In other alternative embodiments, the back of the reflector is provided with a tubular slot 34', and one end or a section of the heat pipe are fitted in the tubular slot 34' to transfer heat by the heat pipe; In this case, the thermally conductive cover 30' is not necessary.

In this embodiment, the heatsink 23' is arranged in the heat dissipation air path, that is, the heatsink 23' is arranged in the air path which communicate the air inlet 60, the fan 25, the air outlet channel 280, and the air outlet 66. The air flow direction in the air path is opposite to the reflector, that is, the direction away from the reflector 32 or the light source 31.

Figure 3:
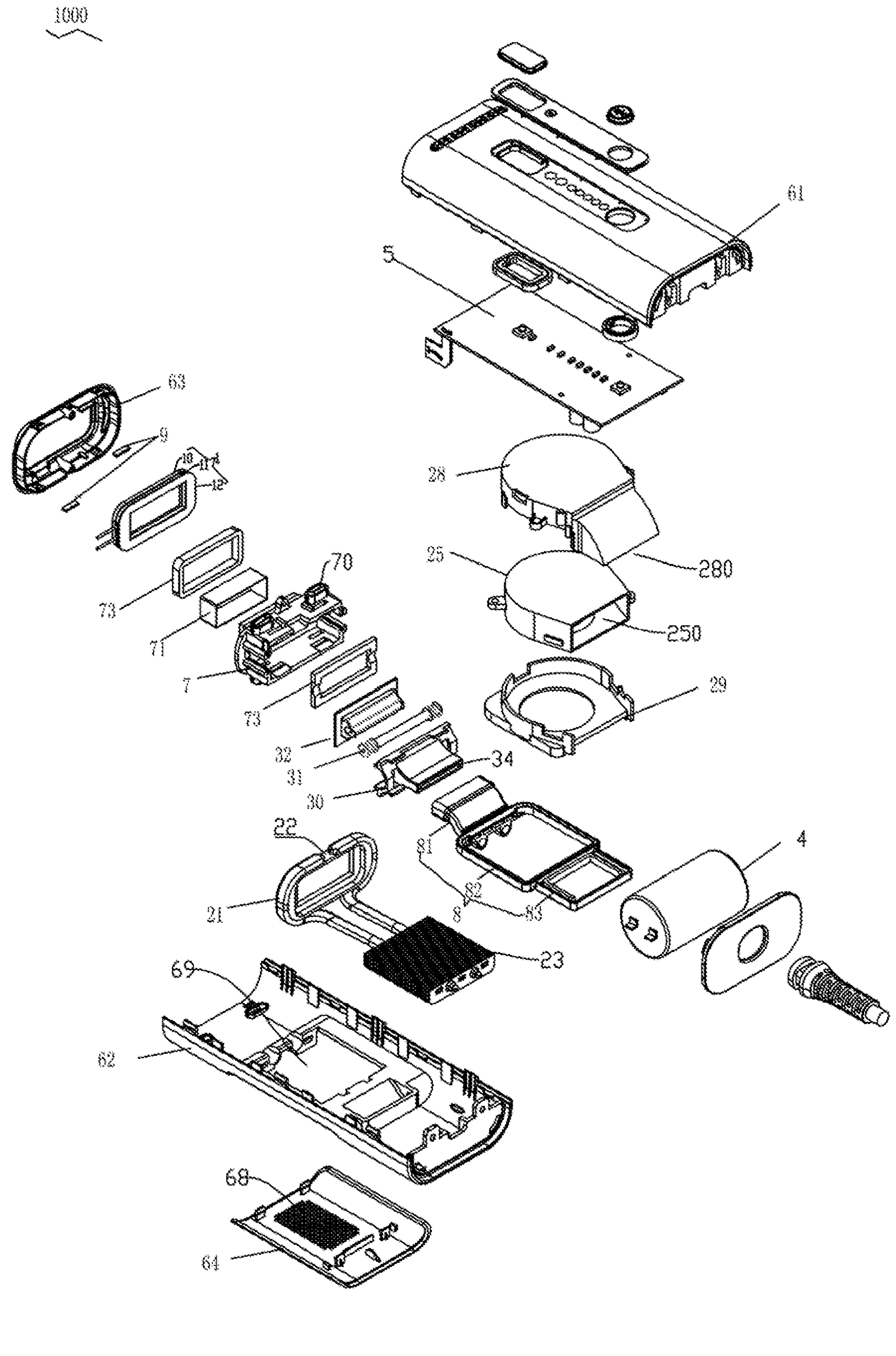
FIG. 3 is an exploded view of FIG. 2 in accordance with the first embodiment of the present invention.
Figure 4:
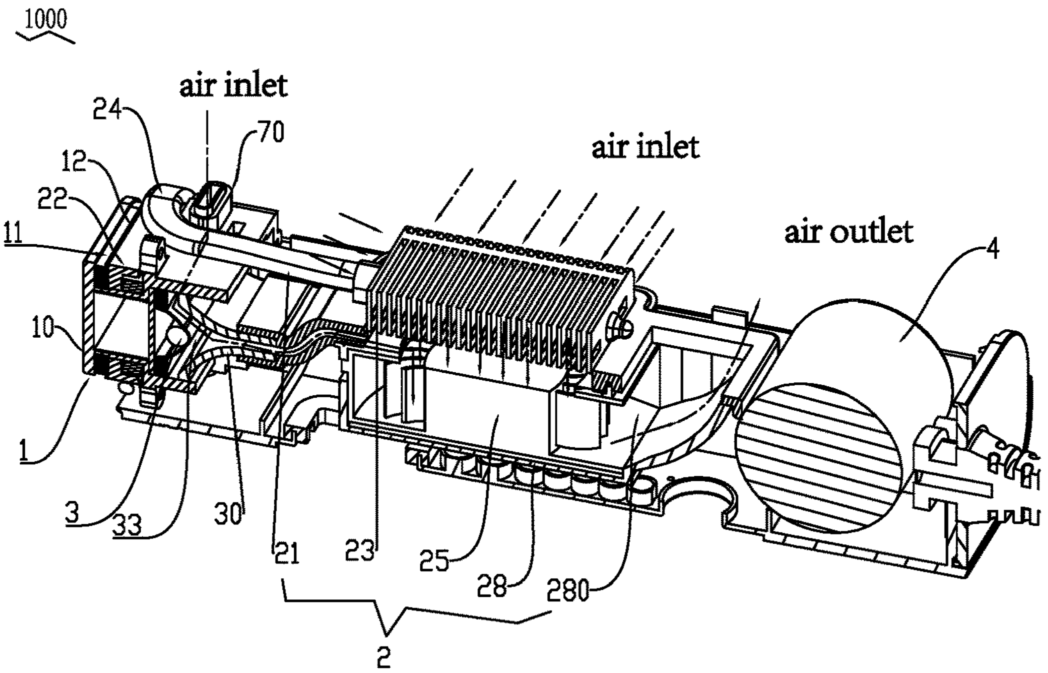
FIG. 4 is a perspective view of the internal structure of the hair removal device in accordance with the first embodiment of the present invention.
Figure 5:
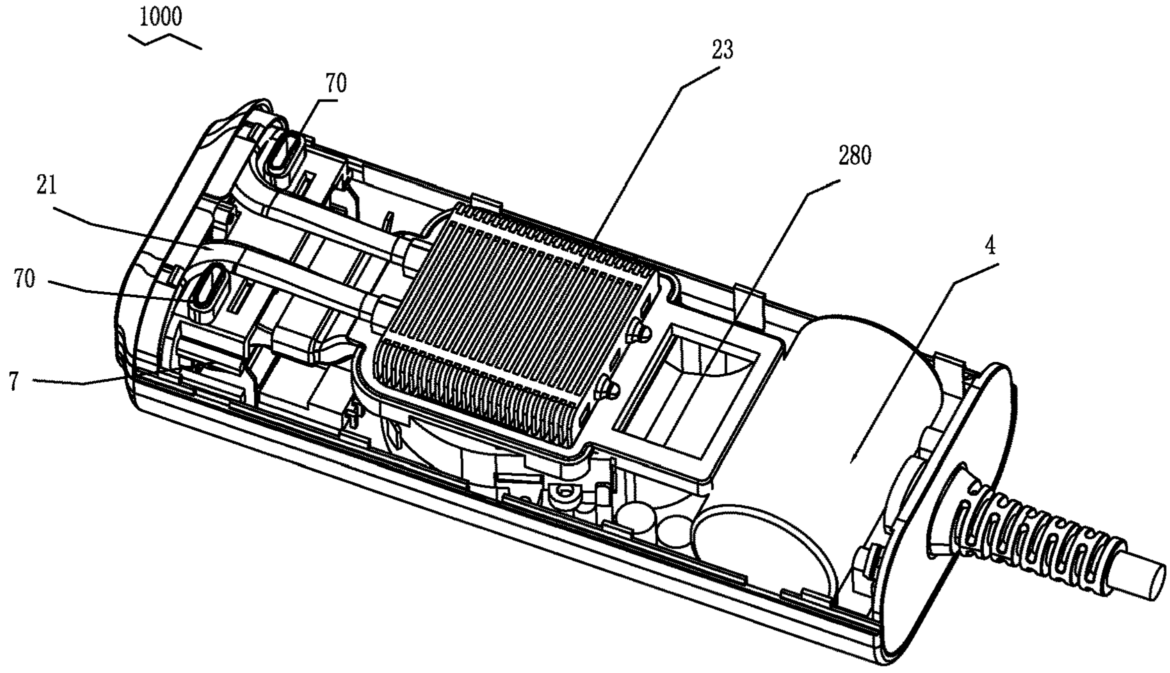
FIG. 5 is a perspective view of the hair removal device after removing part of the housing in accordance with the first embodiment of the present invention.
Figure 6:
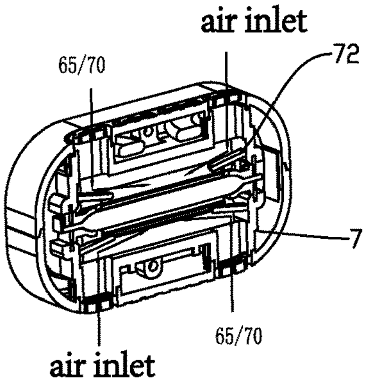
FIG. 6 illustrates a structure of the light source and air ducts for heat dissipation in accordance with the first embodiment of the present invention.
Figure 23:
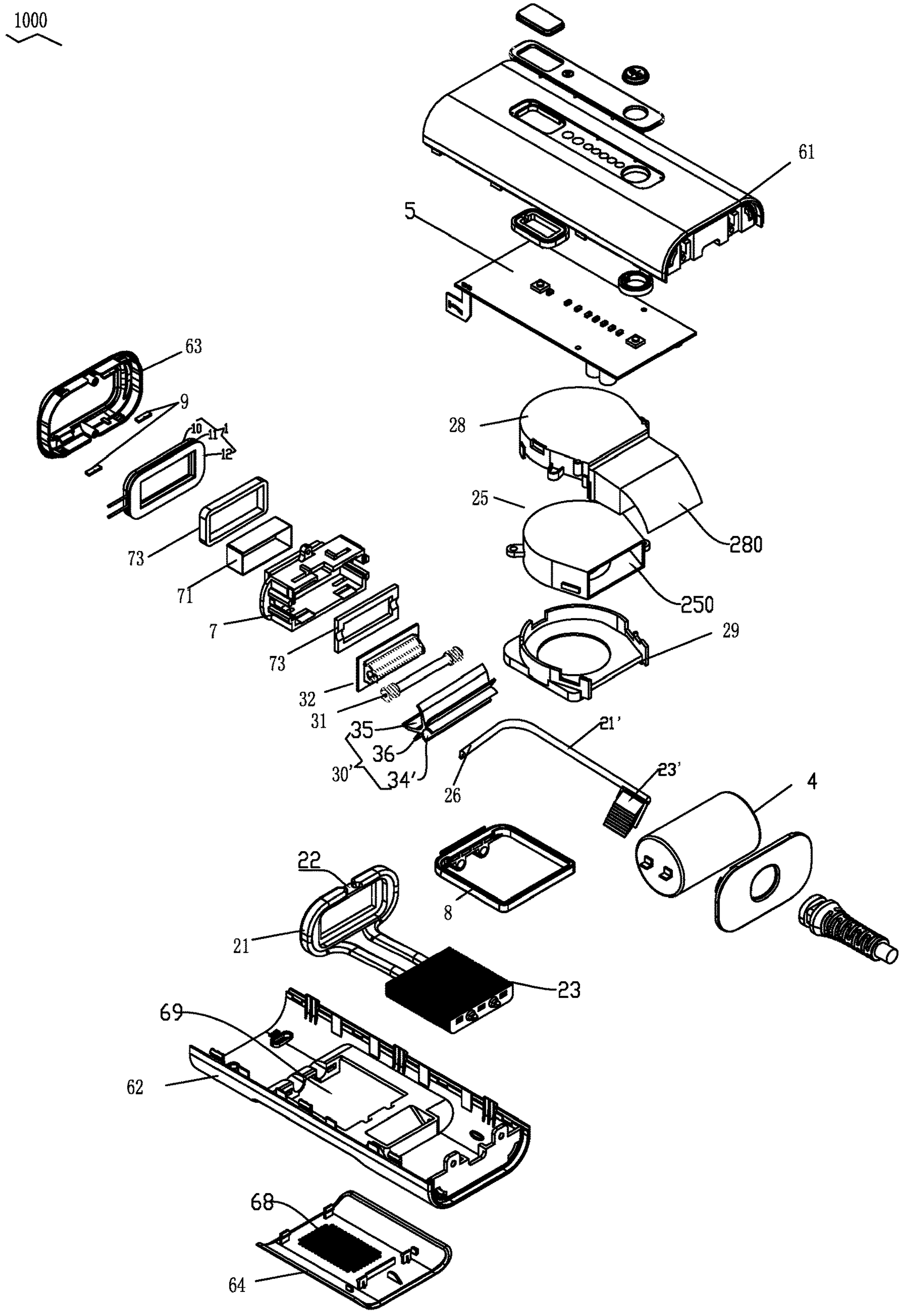
FIG. 23 illustrates an exploded view of the hair removal device in accordance with the second embodiment of the present invention.
Figure 24:
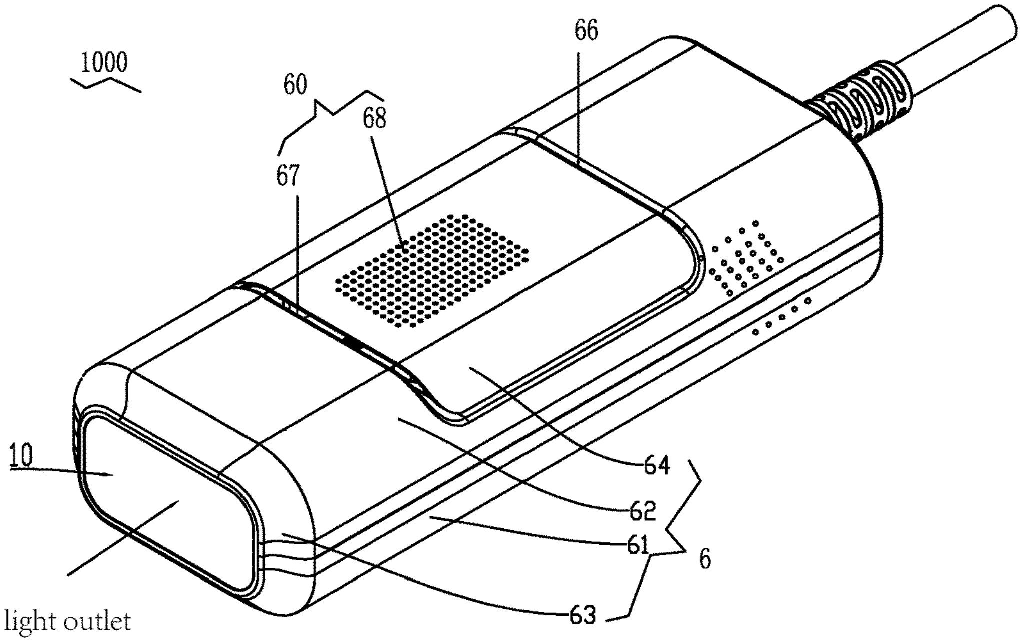
FIG. 24 illustrates a perspective view of the hair removal device in accordance with the second embodiment of the present invention.
Figure 25:
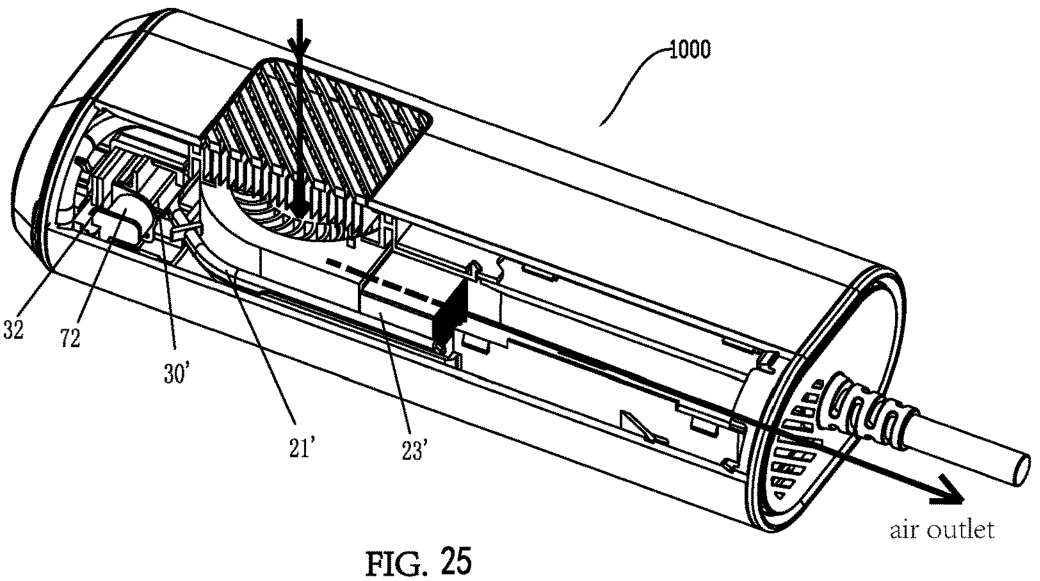
FIG. 25 illustrates an internal structure of the hair removal device in accordance with the second embodiment of the present invention.

In some embodiments, a fan 25 is installed inside the cavity 28 (as shown in FIG. 3, FIG. 7, and FIG. 23), and an air outlet channel 280 is provided at one side of the fan. The air outlet 250 of the fan 25 communicates with the air outlet channel 280, and is in air communication with the air outlet 66 in the housing 6. The fan 25, the air outlet channel 280, and the air outlet 66 in the housing are in air communication with to form a heat dissipation air path. The heatsink 23' is arranged in the air path.

In the present embodiment, the heatsink 23' is arranged in the heat dissipation air path, when the reflector 32 dissipates heat, cooling air may not flow to the reflector 32 or the thermally conductive cover 30', while air from the heatsink 23 for the Peltier cooler flows through the fan 25, blows out to the heatsink 23' of the reflector 32, and flows to the outside of the housing 6. The air outlet 66 can be arranged on both sides of the fan or in the rear of the housing.

It can be understood that the heatsink 23' for the light source and the heatsink 23 for the Peltier cooler can be the same heatsink. The fan of the heat dissipation assembly for the light source assembly can also be separate one from the fan 25.

In this embodiment, the heat dissipation assembly for the light source assembly has advantages that heat dissipation efficiency can be improved, and the first air inlet 65 and the ventilation passages 70 are not necessary, which can improve the waterproof and dustproof of the device.

Various Embodiments of Heat Dissipation Assembly for the Light Source Assembly

Figure 26A:
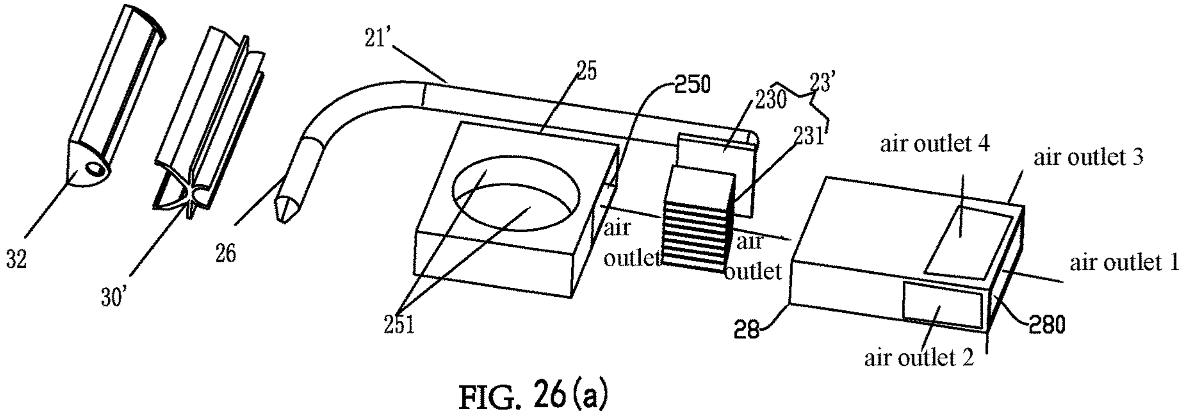
FIGS. 26(*a*)-26(*e*) illustrate the heat dissipation assembly of the light source in accordance with embodiments of the present invention.
Figure 26B:
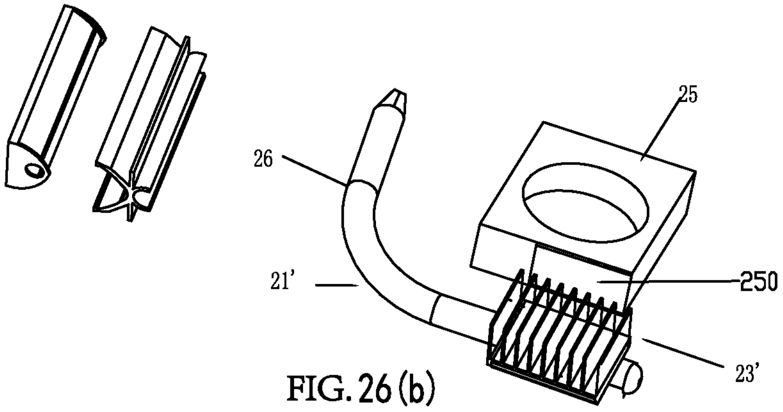
Figure 26C:
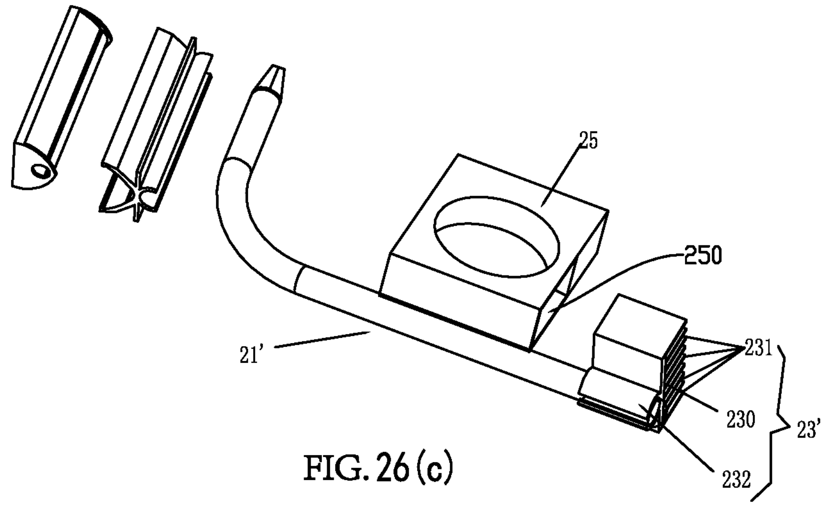
Figure 26D:
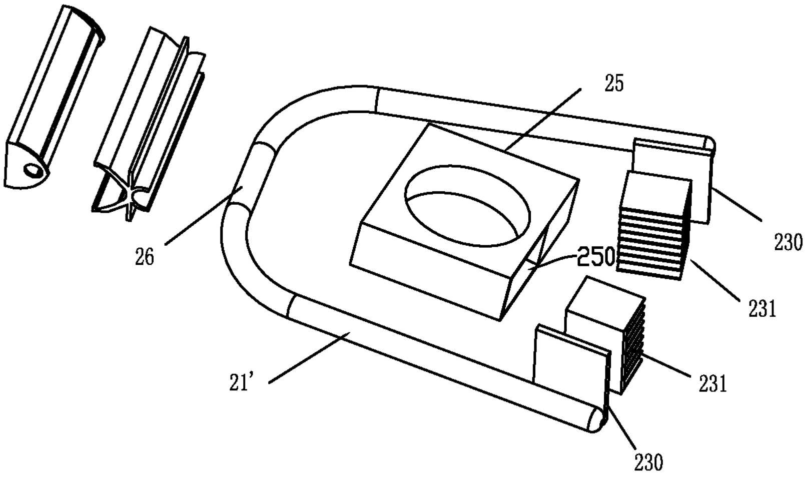
Figure 26:
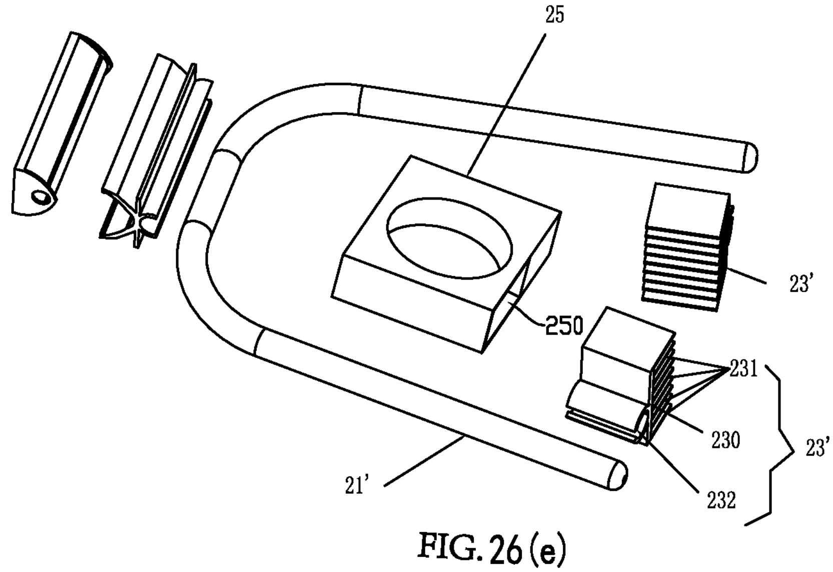

In various embodiments of the heat dissipation assembly for the light source assembly, with reference to FIG. 23 and FIGS. 26(*a*)~26(*e*) again, the cooling system for the light source assembly includes the above-mentioned heat pipe 21' and the heatsink 23', also includes the fan 25 (also for the heat dissipation assembly for the Peltier cooler) in the housing 6. The heatsink 23' includes plate fins, which can be one or more sets of parallel plate fins; or the heatsink 23' includes a thermally conductive base plate 230 and one or more sets of parallel plate fins 231 fixed on one side of thermally conductive base plate 230. A cooling air duct is formed between the two parallel plates. One end or section 26 of the heat pipe 21' is inserted into the tubular slot 34' of thermally conductive cover 30' (or reflector 32). The other end of the heat pipe 21' is fixed (riveted/welded/attached) to the other side of the base plate 230, or inserted (riveted/welded/attached) in one or more sets of parallel plate fins 231 or fixed on the surface of the plate fins, so as to quickly transfer heat from the light source assembly to the heatsink 23' for heat dissipation.

In the two examples shown in FIGS. 26(*a*) and 26(*b*), the heatsink 23' includes a thermally conductive base plate 230 and a set of parallel plate fins 231 fixed on one side of the thermally conductive base plate 230. The heat pipe 21' is bent into an L shape, one end 26 is inserted into the tubular slot 34' of thermally conductive cover 30', and the other end is fixed (riveted/welded/attached) to the other side of thermally conductive base plate 230. The fan 25 with an air inlet 251 is arranged with the heatsink 23 up and down, that is, the heatsink 23 for the Peltier cooler is installed on the top or bottom of the fan 25, and the air ducts of the heatsink 23 for the Peltier cooler is in air communication with the fan through the air inlet 251. The fan provides an air outlet 250. The air inlet 251, the air outlet 250 and the inner side the fan is in air communication. The cavity 28 in this specific example is different from the previous embodiments. The fan 25 is located outside the cavity 28, the cavity 28 is arranged outside the air outlet 250 of the fan 25, and the cavity 28 provides the air outlet channel 280. Air discharged from the air outlet 250 of the fan 25 flows to the air outlet 66 through the air outlet channel 280. The heatsink 23' for the light source is installed between the air outlet 250 of the fan 25 and the air outlet channel 280, and can also be arranged inside the air outlet channel 280. The cooling air ducts of the heatsink 23' for the light source is located between the air outlet. 250 and the air outlet channel 280, so that the air discharged by the fan 25 blows to the surface of the heatsink 23', and the hot air after cooling the heatsink 23' is discharged through the air outlet channel 280 and the air outlet 66. At the end of the air outlet channel 280, a plurality of air outlets can be defined in the cavity 28 corresponding to the air outlet 66 in the housing. It can be understood that the cavity 28 may be a part separately arranged inside the housing of the hair removal device, or may be a part of the housing.

In the embodiment as shown in FIG. 26(*c*), compared with the two embodiments as shown in FIGS. 26(*a*) and 26(*b*), the difference is that a tubular section 232 is provided, for example, by being integrated or soldered, on one side of thermally conductive base plate 230. The end of heat pipe 21' is fitted in the thermally conductive tube 2 for heat dissipation. A set of parallel cooling fins 231 are set on the other side of the thermally conductive base plate 230 for heat dissipation. The heatsink 23' is located in the air path outside the air outlet 250, and the cooling air ducks of heatsink 23' communicate the cooling air path between fan 25 and the air outlet 66.

In the embodiment as shown in FIG. 26(*d*), heat pipe 21' is bent into a U shape, and a section 26 of the integral U-shaped pipe is inserted into the tubular slot 34' of thermally conductive cover 30'. Each of opposite ends of heat pipe 21' is fixed (riveted/welded/attached) with one thermally conductive base plate 230. A set of parallel plate fins 231 is welded to one side of each thermally conductive base plate 230, that is, each of opposite ends of heat pipe 21' respectively connect a heatsink 23', and the two heatsinks 23' are placed opposite to each other, and are located in the cooling air path outside the outlet hole 250 of the fan.

In the embodiment as shown in FIG. 26(*e*), the difference with respect to the embodiment as shown in FIG. 26(*d*) is that a tubular section 232 is provided, for example, by being integrated or soldered, on one side of each thermally conductive base plate 230. Each end of heat pipe 21' is fitted in the corresponding heat pipe 232. A set of parallel cooling fins 231 are set on the other side of each thermally conductive base plate 230 for heat dissipation.

Other structures of the hair removal device in these embodiments are similar to the first embodiment of the hair removal device, where the light source assembly 3 is installed in the light source frame 7, and the light source frame 7 is installed in the head. The head and the light source frame 7 are connected by a reflective cover 71, and the pulsed light emitted from the light source assembly 3 is transmitted to the head through the reflective cover 71 for hair removal. In this embodiment, the sealing member 8 may be an annular sealing ring, which is installed around the air inlet 251 at the top or bottom of the fan 25 to prevent air leakage.

Third Embodiment of the Hair Removal Device

In foregoing each embodiment, the cold side 10 of the Peltier cooler 1 is made of transparent materials, and the cold side preferably is a transparent crystal which provides a hair removal surface in contact with skin. The hair removal surface is located at the front end of the hair removal device, that is, at the front end of the head. Preferably, the transparent crystal cold side (or transparent cold side) can provide one entire side surface as the hair removal surface, thereby forming a cooling effect on the whole front-end surface. The advantage of whole-surface cooling is that: the skin can be pre-cooled during hair removal, and can continue to be cooled after hair removal so as to reduce burning feeling after hair removal, which can prolong the time for cooling the skin.

Figure 27:
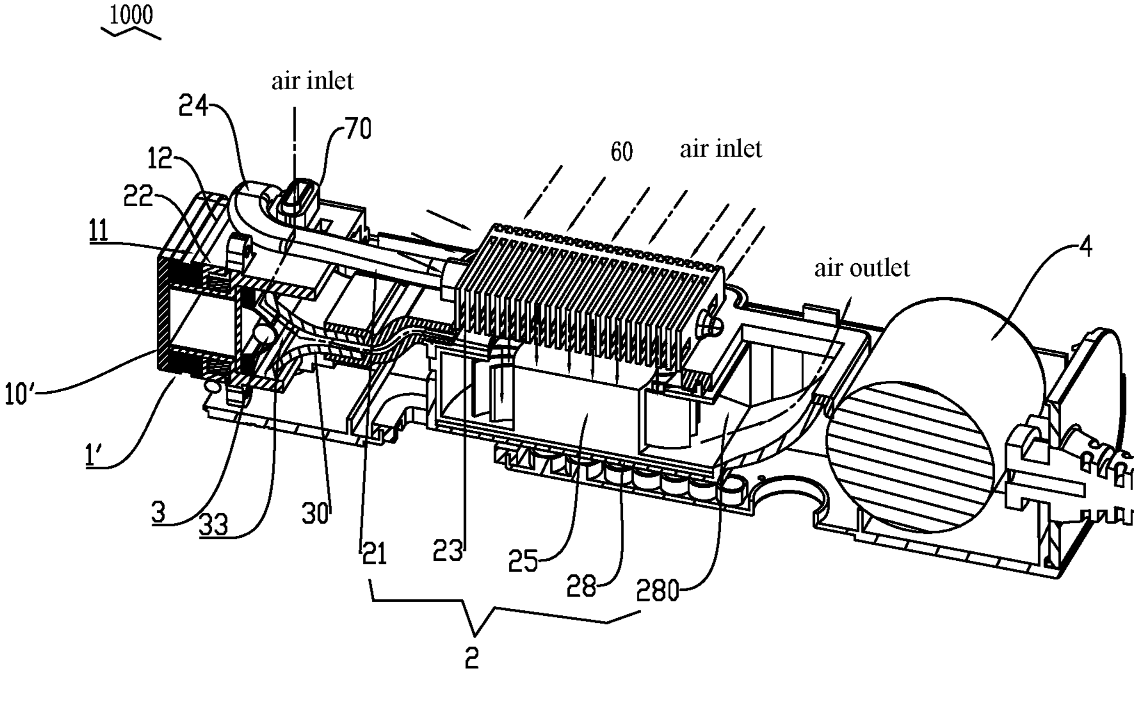
FIG. 27 illustrates an internal structure of the hair removal device in accordance with a third embodiment of the present invention.
Figure 28:
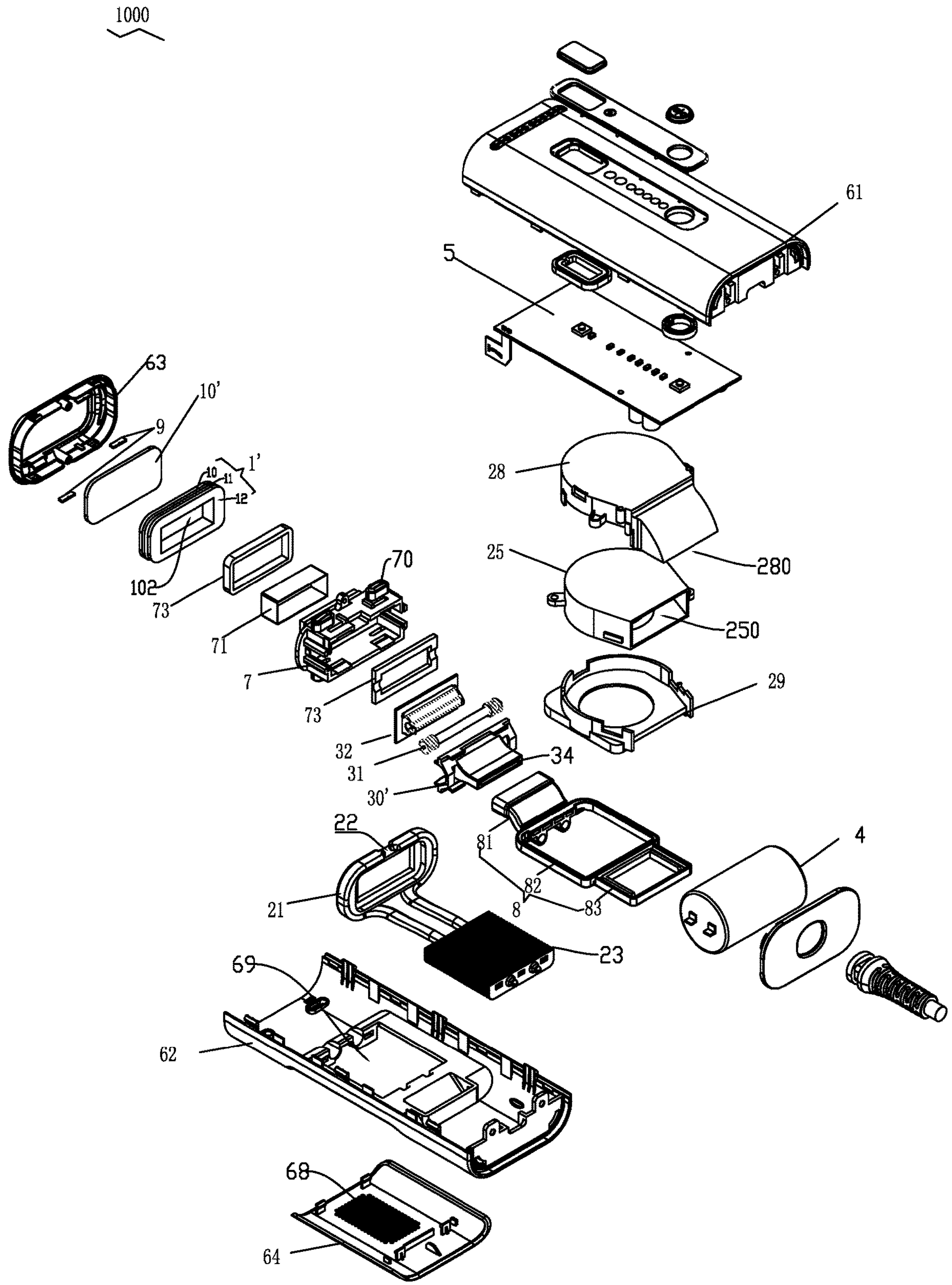
FIG. 28 is an exploded view of the heat dissipation assembly of the Peltier cooler in accordance with the third embodiment of the present invention.

With reference to FIGS. 27-28, same as previous embodiments, the hair removal device 1000 of present embodiment comprises a head, a heat dissipation assembly 2, a light source assembly 3, a heat dissipation assembly for the light source assembly, a power supply unit 4, and a control circuit board 5. The heat dissipation assembly 2, the light source assembly 3, the heat dissipation assembly for the light source assembly, the power supply unit 4 and the control circuit board 5 are installed in the housing 6 of the hair removal device. The control circuit board 5 is electrically connected with the light source assembly 3 and the power supply unit 4 to control the light source to emit pulsed light for hair removal. The power supply unit 4 is used to supply power to the light source assembly 3. In this embodiment, the head for hair removal of the hair removal device 1000 is equipped with a cooler 1' and a transparent crystal (or transparent) 10'. The transparent crystal (or transparent) 10' provides an entire front surface of the head (or hair removal device) as a hair removal surface in direct contact with the skin. The control circuit board 5 controls the power supply unit 4 to excite the light source assembly 3 to emit pulsed light, and the pulsed light transmits the hair removal surface for depilatory treatment. The heat dissipation assembly 2 is connected to cooler 1' for cooling. The housing 6 defines a first air inlet 60 and an air outlet 66. The hair removal device 1000 can also be provided with a power cord and/or a charging interface to be connected to an external power source.

Compared with the above-mentioned embodiments, the hair removal device in this embodiment has a different head, where the transparent crystal (or transparent body) 10' provides the hair removal surface in contact with the skin. Preferably, the transparent crystal (or transparent body) 10' provides the entire surface of the hair removal surface, thereby forming a cooling effect on the entire front end of the head. The transparent crystal (or transparent body) 10' is cooled by the cooler 1' attached on the back of the transparent crystal. The head housing 63 is an annular housing, and the transparent crystal (or transparent body) 10' is clamped and installed in the annular housing. The cooler 1' is also fastened in the head housing 63, and attached to the back of the transparent crystal (or transparent medium body) 10'. There may be one cooler 1' installed on one side or more sides of the transparent crystal (or transparent body) 10'. The cooler 1' installed in the head for hair removal can be a cooler of prior art to cool the transparent crystal (or transparent) hair removal surface, and the heat dissipation assembly 2 of the aforementioned embodiment can be used for the cooler 1' to dissipate heat.

In accordance with a preferable embodiment, the cooler 1' installed in the depilation head is a Peltier cooler. The transparent crystal (or transparent) surface are cooled using the Peltier cooler. Specifically, a transparent crystal (or transparent body) 10' is attached on a cold side of the Peltier cooler in the head, and the transparent crystal (or transparent body) 10' is directly used as the hair removal surface in contact with the skin. Preferably, the transparent crystal (or transparent body) 10' provides one side surface as the hair removal surface, thereby forming a cooling effect on the entire front end of the head. The transparent crystal (or transparent body) 10' is cooled by the Peltier cooler 1' attached to its back. The head housing 63 is an annular shell, and the transparent crystal (or transparent body) 10' is clamped and installed in the annular housing, and the Peltier cooler 1' is also clamped in the head housing 63. The cold side 10 is attached to the back of the transparent crystal (or transparent body) 10'.

The Peltier cooler 1' has a light-transmitting region 102. It can be understood that the Peltier cooler 1' can adopt the above-mentioned Peltier cooler of which the light-transmitting region 102 is provided by a transparent crystal cold side. In this embodiment, the Peltier cooler 1' is annular-shaped, and the center hole forms the light-transmitting region 102. The Peltier cooler 1' comprises a semiconductor pillar layer 11, and a hot side 12 and a cold side 10 at both ends of the semiconductor pillar layer. The Peltier cooler 1' is annular-shaped, correspondingly, the hot side 12 and the cold side 10 and the semiconductor pillar layer 11 are all annular-shaped. The annular hot side 12 and the annular cold side 10 are layered in alignment and soldered at opposite ends of the annular semiconductor pillar layer 11. The center hole forms the light-transmitting region 102. The hot side 12 and the cold side 10 can be ceramic substrates to form the ceramic hot side and the ceramic cold side, and other materials in the prior art can also be used for the cold side and hot side. The cold side 10 is attached on the back of the transparent crystal (or transparent body) 10' to cool the transparent crystal (or transparent body) 10'. The transparent crystal (or transparent body) 10' covers the entire front surface of the cold side 10.

Transparent crystal (or transparent body) 10' and Peltier cooler 1' are fixed using the head housing 63, and transparent crystal (or transparent body) 10' is positioned at a front end of the head (hair removal device), and used as a hair removal surface. The head housing 63 is tightly assembled with the front ends of the upper and lower housings 61, 62, and is tightly assembled with the light source frame 7. The head can be further fixed by fasteners such as screws, positioning columns or buckle structures. The head housing 63 is assembled with the upper and lower housings 61, 62 and the light source frame 7.

The Peltier cooler 1' is electrically connected with the control circuit board 5. The control circuit board 5 controls the light source assembly 3 to emit pulsed light that transmits through the light-transmitting region 102 of the Peltier cooler 1', further transmits through the hair removal surface of the transparent crystal (or transparent body) 10', and burns hairs on the skin in contact with the transparent crystal (or transparent) surface.

The Peltier cooler 1'is connected with the heat dissipation assembly 2, and heat from the Peltier cooler is transported to the heat dissipation assembly from the hot side 12 to dissipate heat. The heat dissipation assembly 2 includes heat pipes 21 and a heatsink 23 connected to the heat pipes 21.

Other structure of the hair removal device as shown in FIGS. 27-28 in this embodiment is the same as the hair removal device in the first embodiment, or the same as the hair removal device in the second embodiment, or the same as the existing hair removal device, which will not be repeated herein, but the disclosure of which are incorporated by reference herein.

In some embodiments, at least two sensors 9 are installed in the head of the hair removal device 1000 to detect whether the transparent crystal working surface is completely or almost completely covered by skin so as to turn on/off the light source. Wherein, the two sensors 9 are installed at the diagonal corners of the edge of the hair removal surface 10. The sensor 9 is connected with the control circuit board 5.

In the description of the present invention, it should be understood that the terms "length", "width", "upper", "lower", "front", "rear", "left", "right", "vertical The orientations or positional relationships indicated by "straight", "horizontal", "top", "bottom", "inner", "outer", etc. are based on the orientation or positional relationship shown in the drawings, and are only for the convenience of describing the present invention and simplifying the description, but does not express or imply that the device or member referred to must have a specific orientation, be constructed and operated in a specific orientation, and therefore should not be construed as limiting the invention.

Although the embodiment of the present invention has been shown and described, for those of ordinary skill in the art, it can be understood that various changes can be made to this embodiment without departing from the principle and spirit of the invention, Modifications, replacements and variations shall all belong to the scope of the present invention; the protection scope of the present invention is defined by the appended claims and their equivalent scope.

What is claimed is:

1. A hair removal device, comprising:

a head for hair removal;

a light source assembly;

a power supply unit for the light source assembly;

a Peltier cooler;

a first heat dissipation assembly for cooling the Peltier cooler; and a control circuit board for controlling the light source assembly to emit light;

wherein the head for hair removal is equipped with a transparent body to form a transparent working surface in contact with skin for hair removal; the light emitted from the light source assembly is transmitted from the transparent body to perform hair removal;

the Peltier cooler comprises a semiconductor pillar layer, and a hot side and a cold side are respectively fixed on opposite sides of the semiconductor pillar layer;

the hot side of the Peltier cooler is connected to the first heat dissipation assembly for heat dissipation;

the transparent body is the cold side of the Peltier cooler; or, the cold side of the Peltier cooler is attached to the transparent body; whereby the transparent body is cooled and is able to provide a cooling effect to skin or pre-cooling skin;

the Peltier cooler has a light-transmitting region, which is used for light transmission for hair removal; the light-transmitting region is a hollow region in the Peltier cooler, and/or, the light-transmitting region is provided by the transparent body of the Peltier cooler;

the hair removal device comprises a housing, and the light source assembly, the power supply unit, the control circuit board and the first heat dissipation assembly are installed in the housing; the housing defines air inlets and air outlets;

the light source assembly comprises a second heat dissipation assembly; the second heat dissipation assembly comprises a heat pipe, a heatsink, and a fan; the heat pipe is thermally connected between the light source assembly and the heatsink, and used for transferring heat from the light source assembly to the heatsink; the heatsink is arranged in an air path which is in air communication with the air inlets, the fan and the air outlets; and the heatsink is cooled through the air path;

the light source assembly comprises a light source and a reflector outside the light source;

the reflector is provided with a tubular slot, and a section of the heat pipe is fitted in the tubular slot so as to transfer heat from the reflector to the heat pipe; or, the light source assembly further comprises a thermally conductive cover with one side thereof attached to the reflector, and the other side provided with a tubular slot; a section of the heat pipe is fitted in the tubular slot so as to transfer heat to the heat pipe.

2. The hair removal device as claimed in claim 1, wherein:

the transparent body is installed in a head housing;

the first heat dissipation assembly comprises a heat pipe, a heatsink and the fan; the heatsink of the first heat dissipation assembly is arranged in an air path in communication with the air inlets, the fan and the air outlets for heat dissipation;

the heat pipe of the first heat dissipation assembly is connected with the hot side of the Peltier cooler and the heatsink of the first heat dissipation assembly, and is used to transport heat from the hot side to the heatsink for heat dissipation.

3. The hair removal device as claimed in claim 1, wherein:

the control circuit board controls the light source assembly to emit light which transmits through the light-transmitting region of the Peltier cooler, further transmits through the transparent working surface for hair removal on the skin in contact;

the semiconductor pillar layer, the hot side and the cold side of the Peltier cooler together define the hollow region;

the Peltier cooler is annular with the hollow region inside as the light-transmitting region;

the Peltier cooler is fixed in a head housing, and is attached to a back of the transparent body.

4. The hair removal device as claimed in claim 1, wherein the transparent body is a transparent crystal to form a transparent crystal cold side of the Peltier cooler; the transparent crystal connects one or more sets of the semiconductor pillar layers each with one hot side connected thereto; the Peltier cooler has the light-transmitting region provided by the transparent crystal to form the transparent working surface.

5. The hair removal device as claimed in claim 1, wherein the Peltier cooler is annular; the semiconductor pillar layer is annular of which electronic components are arranged in an annular region; the hot side and the cold side are annular corresponding to the semiconductor pillar layer with center holes thereof aligned to form the light-transmitting region.

6. The hair removal device as claimed in claim 1, wherein the head is equipped with at least two sensors for determining whether the working surface is completely or almost completely covered by skin so as to turn on/off the light source; the two sensors are installed at opposite corners along a diagonal line of the working surface.

7. A Peltier cooler, comprising:

one or more semiconductor pillar layers, each connected with one hot side; and the hot side and a cold side, connected with opposite ends of the semiconductor pillar layer;

wherein the cold side is a transparent crystal to form a transparent crystal cold side; the transparent crystal connects the one or more semiconductor pillar layers each connected with the one hot side; the Peltier cooler has a light-transmitting region provided by the transparent crystal to form a cooling working surface of a hair removal device to provide a cooling effect to skin or pre-cooling skin in contact with the working surface;

the hot side is connected to a heat dissipation assembly for heat dissipation; the heat dissipation assembly comprises a heat pipe and a heatsink connected to the heat pipe; the heat pipe directly contacts the hot side or connects the hot side through a thermally conductive member; the heat pipe is installed on or inserted in the heatsink;

one end of the thermally conductive member or the heat pipe is adapted for and contacts with the hot side; the heat pipe forms a ring, and the thermally conductive member is fitted in the ring; the heatsink is one or more of: a plate fin heatsink, plate fins, or thermally conductive plates.

8. The Peltier cooler as claimed in claim 7, wherein the one or more semiconductor pillar layers each connected with one hot side are arranged on sides of the transparent crystal;

the hot side and the transparent crystal cold side are soldered with the semiconductor pillar layer.

9. The Peltier cooler as claimed in claim 7, wherein the semiconductor pillar layer is connected with positive and negative electrodes; the transparent crystal cold side covers the semiconductor pillar layer; the semiconductor pillar layer is set between the hot side and the transparent crystal cold side.

10. The Peltier cooler as claimed in claim 7, wherein the one or more semiconductor pillar layers each connected with one hot side are arranged on one side, opposite two sides or multiple sides of the transparent crystal; or, the semiconductor pillar layer is annular with electronic components arranged in an annular region; the hot side is annular, and is fixed with one side of the semiconductor pillar layer; the transparent crystal cold side is fixed with the other side of the semiconductor pillar layer; a hollow region of the annular semiconductor pillar layer, a hollow region of the annular hot side, and together with the transparent crystal forms the light-transmitting region.

11. A hair removal device, comprising:

a head for hair removal, equipped with a Peltier cooler;

a light source assembly;

a power supply unit, supplying power to the light source assembly; and a control circuit board, controlling the light source assembly to generate light;

wherein the Peltier cooler comprises:

one or more semiconductor pillar layers, each connected with one hot side; and the hot side and a cold side, connected with opposite ends of the semiconductor pillar layer;

the cold side is a transparent crystal to form a transparent crystal cold side which is used as a working surface in contact with skin; the transparent crystal connects the one or more semiconductor pillar layers each connected with one hot side, and provides a light-transmitting region:

the hot side is connected to a heat dissipation assembly for heat dissipation; the heat dissipation assembly comprises a heat pipe and a heatsink connected to the heat pipe; the heat pipe directly contacts the hot side or connects the hot side through a thermally conductive member; the heat pipe is installed on or inserted in the heatsink;

one end of the thermally conductive member or the heat pipe is adapted for and contacts with the hot side; the heat pipe forms a ring, and the thermally conductive member is fitted in the ring; the heatsink is one or more of: a plate fin heatsink, plate fins, or thermally conductive plates.

12. The hair removal device as claimed in claim 11, wherein the heat dissipation assembly is arranged in the hair removal device to dissipate heat from the hot side of the Peltier cooler; the heat dissipation assembly further comprises a fan; the hair removal device comprises a housing, the light source assembly, the power supply unit, the control circuit board, and the heat dissipation assembly are installed in the housing; the housing defines air inlets and air outlets; the air inlets, air ducts of the heatsink, the fan, and the air outlets are in air communication to form a first air path; by starting the fan, cold air enters from the air inlets, and takes heat from the heatsink to form hot air, hot air is discharged by the fan through the air outlets to outside for cooling the heatsink.

13. The hair removal device as claimed in claim 12, wherein the air inlets defined in the housing, the light source assembly, the fan, and the air outlets are in air communication to form a second air path; by starting the fan, cold air enters from the air inlets, and takes heat from the light source assembly to form hot air; hot air is discharged by the fan from the air outlet to outside so as to cool the light source assembly; the air inlets comprise a first air inlet in the housing corresponding to the heatsink, and a second air inlet in the housing corresponding to the light source assembly; the first air inlet is used for introducing air to the first air path; and the second air inlet is used for introducing air to the second air path.

* * * * *